(12) United States Patent
Jayant

(10) Patent No.: US 9,370,368 B2
(45) Date of Patent: Jun. 21, 2016

(54) DEVICE FOR DISPENSING, LOOPING AND TYING LIGATURES

(76) Inventor: Ashok Kumar Jayant, Delhi (IN)

(*) Notice: Subject to any disclaimer, the term of this patent is extended or adjusted under 35 U.S.C. 154(b) by 749 days.

(21) Appl. No.: 12/521,731

(22) Filed: Jun. 29, 2009

(65) Prior Publication Data

US 2010/0318105 A1  Dec. 16, 2010

Related U.S. Application Data

(63) Continuation-in-part of application No. PCT/IN2007/000614, filed on Dec. 28, 2007.

(30) Foreign Application Priority Data

Dec. 29, 2006 (IN) .......................... 2829/DEL/2006

(51) Int. Cl.
*A61B 17/04* (2006.01)
*A61B 17/12* (2006.01)
*A61B 17/06* (2006.01)

(52) U.S. Cl.
CPC ....... *A61B 17/12013* (2013.01); *A61B 17/0485* (2013.01); *A61B 17/06123* (2013.01); *A61B 2017/0475* (2013.01); *A61B 2017/0608* (2013.01); *A61B 2017/06052* (2013.01)

(58) Field of Classification Search
CPC ...................... A61B 17/12013; A61B 17/0483; A61B 17/0469; A61B 17/0485; A61B 17/06123; A61B 2017/06019; A61B 2017/06052; A61B 2017/0608
USPC .......................................... 606/139, 144–148
See application file for complete search history.

(56) References Cited

U.S. PATENT DOCUMENTS

| | | | | | |
|---|---|---|---|---|---|
| 2,348,218 | A | * | 5/1944 | Karle | 606/146 |
| 2,414,746 | A | * | 1/1947 | Karle | 606/146 |
| 3,877,434 | A | | 4/1975 | Ferguson et al. | |
| 4,224,947 | A | * | 9/1980 | Fukuda | 606/146 |
| 4,935,027 | A | * | 6/1990 | Yoon | 606/146 |
| 5,112,344 | A | * | 5/1992 | Petros | 606/148 |
| 5,207,693 | A | * | 5/1993 | Phillips | 606/146 |
| 5,207,694 | A | | 5/1993 | Broome | |
| 5,334,199 | A | * | 8/1994 | Yoon | 606/144 |
| 5,350,385 | A | * | 9/1994 | Christy | 606/139 |
| 5,486,186 | A | * | 1/1996 | Yoon | 606/148 |
| 5,562,686 | A | * | 10/1996 | Sauer et al. | 606/144 |
| 5,571,119 | A | * | 11/1996 | Atala | 606/146 |
| 5,571,120 | A | | 11/1996 | Yoon | |
| 5,643,292 | A | * | 7/1997 | Hart | 606/144 |
| 5,653,716 | A | * | 8/1997 | Malo et al. | 606/139 |

(Continued)

OTHER PUBLICATIONS

International Search Report and Written Opinion for PCT/IN2007/000614, mailed May 8, 2008, 12 pages.

*Primary Examiner* — Darwin Erezo
*Assistant Examiner* — Shaun L David
(74) *Attorney, Agent, or Firm* — Hamre, Schumann, Mueller & Larson, P.C.

(57) ABSTRACT

A device for dispensing, looping and tying ligature comprising a housing, a spool, a cannula, a lock-unlock mechanism and a snare is disclosed. The spool has surgical or non surgical thread/cord wound thereon in a plurality of turns. The spool is rotatably and removably mounted in the housing. The cannula is removably and rotatably mounted to the base of the housing. The lock-unlock mechanism is configured to control dispensing of the thread/cord. The snare includes a steel wire to form a Y shape or hook shape with a narrow pointed tip to thread the cannula.

19 Claims, 16 Drawing Sheets

(56) References Cited

U.S. PATENT DOCUMENTS

| | | | |
|---|---|---|---|
| 5,665,096 A * | 9/1997 | Yoon | 606/139 |
| 5,693,059 A * | 12/1997 | Yoon | 606/139 |
| 5,713,910 A * | 2/1998 | Gordon et al. | 606/144 |
| 5,720,754 A * | 2/1998 | Middleman et al. | 606/127 |
| 5,749,879 A * | 5/1998 | Middleman et al. | 606/139 |
| 6,494,887 B1 * | 12/2002 | Kaladelfos | 606/148 |
| 7,666,203 B2 * | 2/2010 | Chanduszko et al. | 606/185 |
| 7,842,046 B1 * | 11/2010 | Nakao | 606/144 |
| 2010/0318105 A1 * | 12/2010 | Jayant | 606/148 |

* cited by examiner

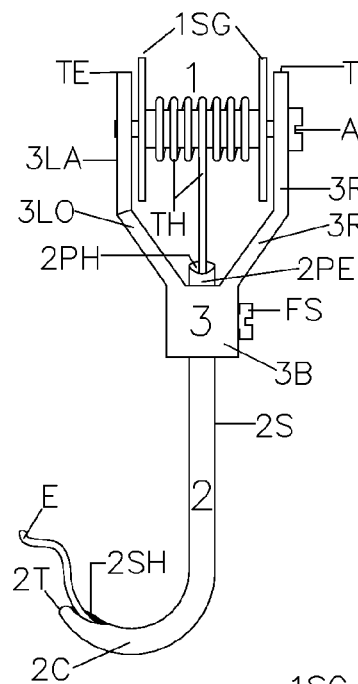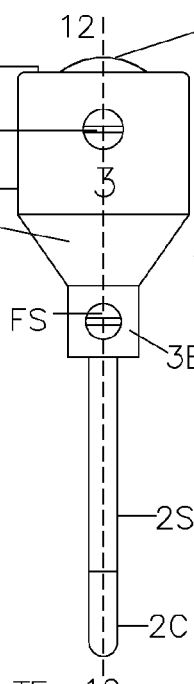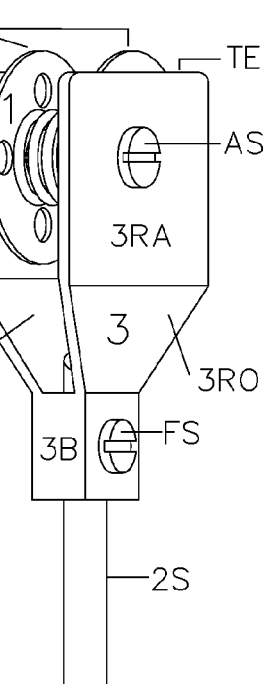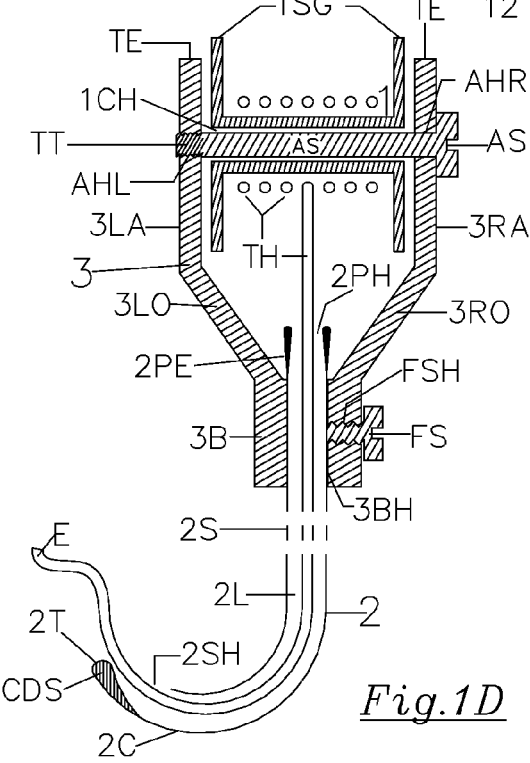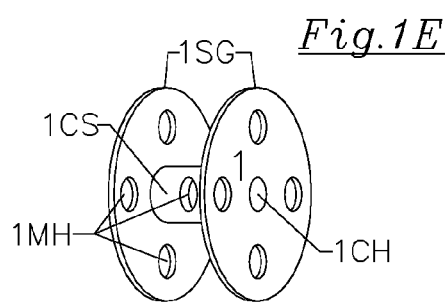

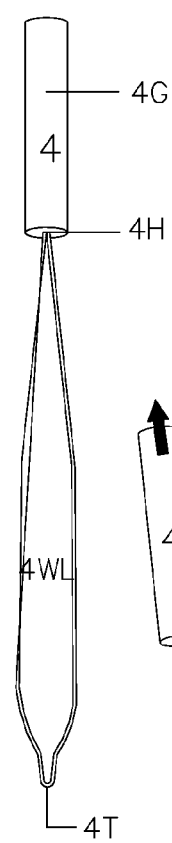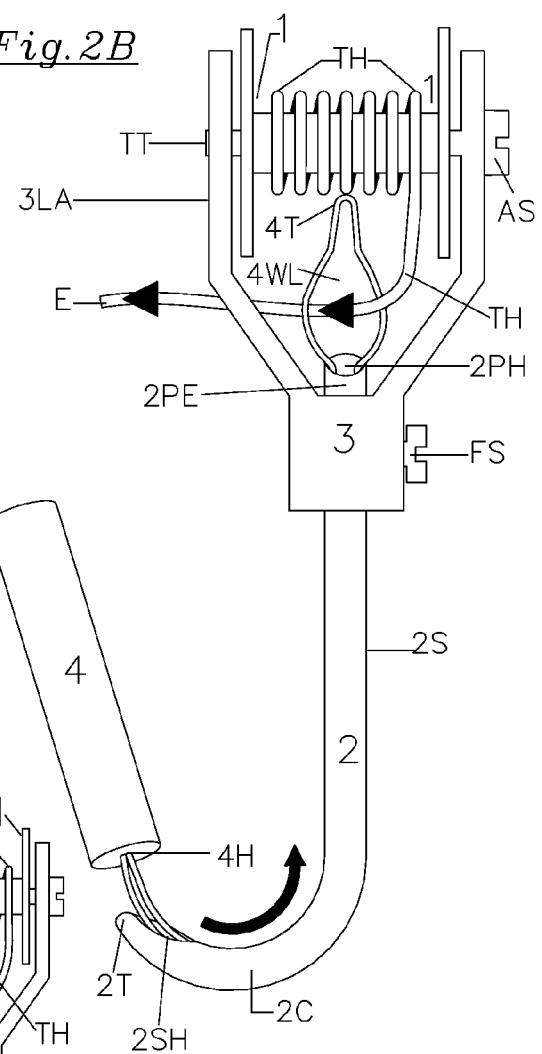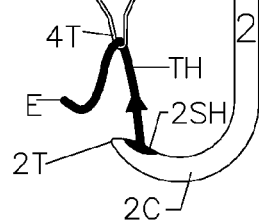

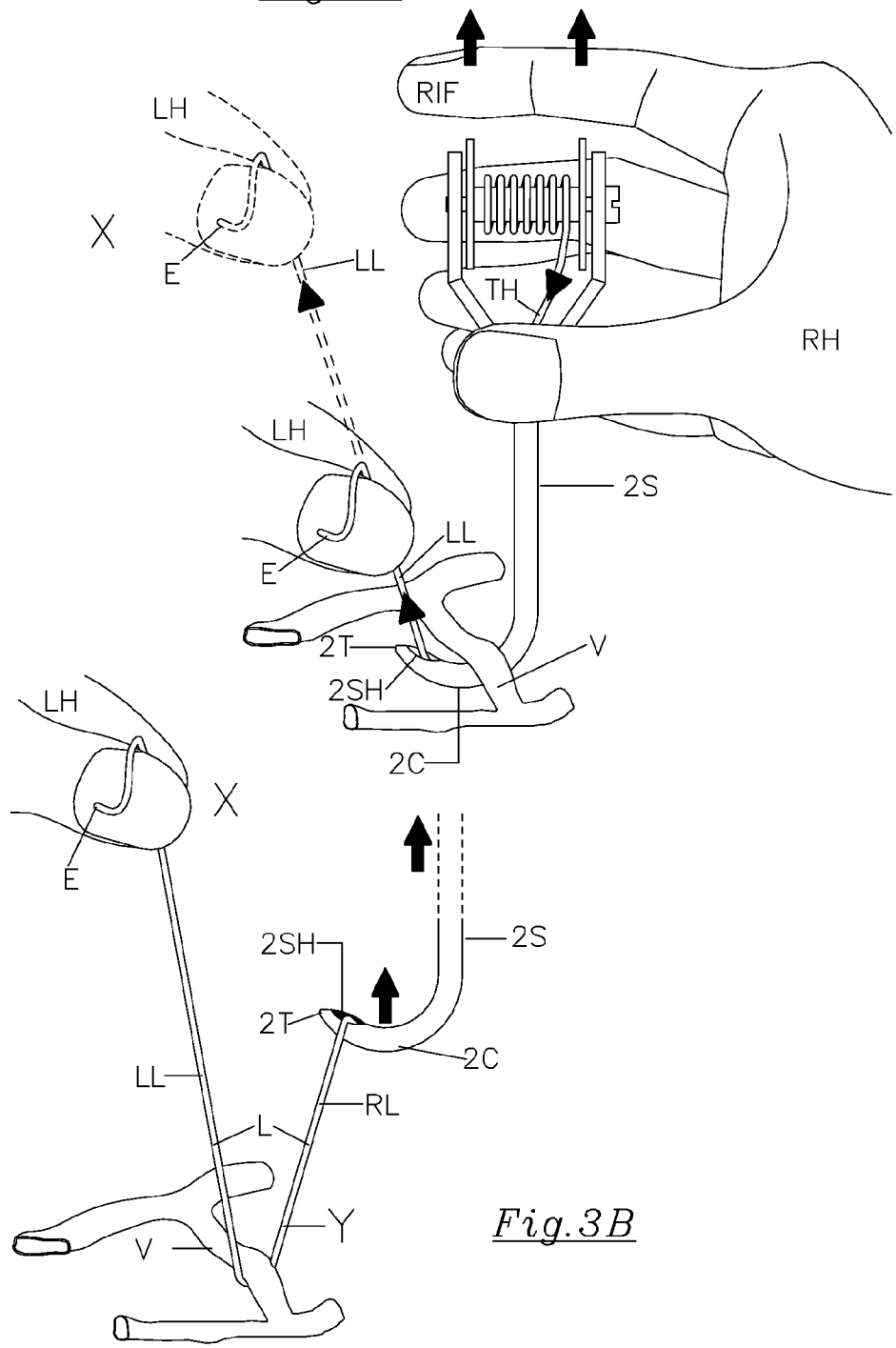

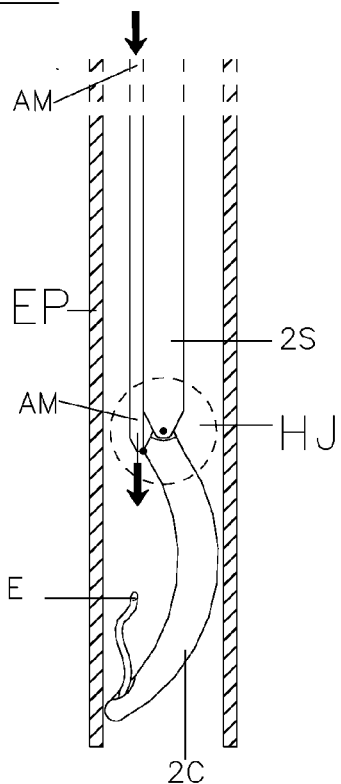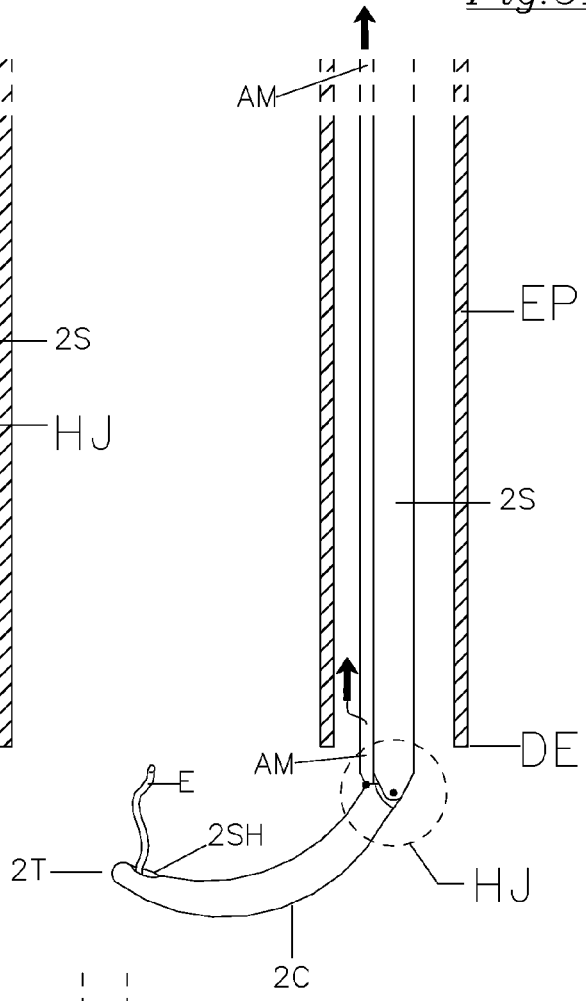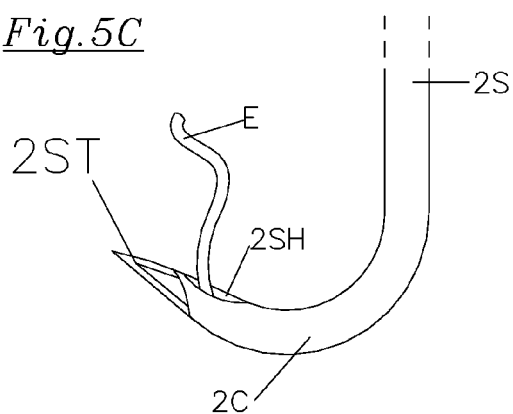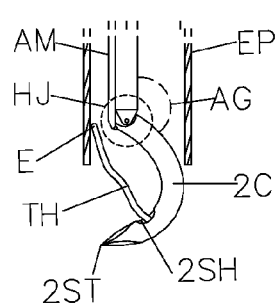

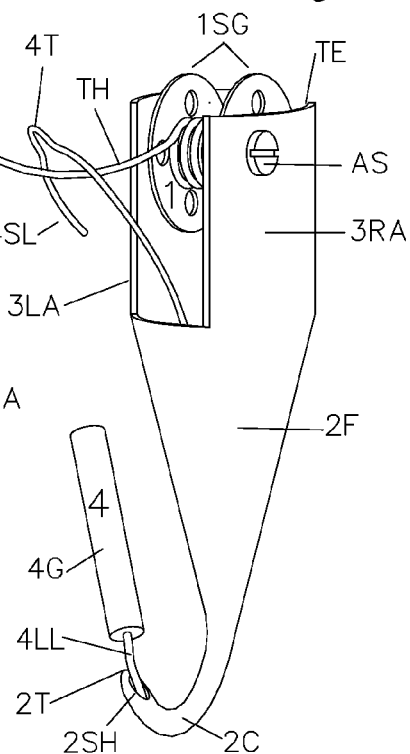
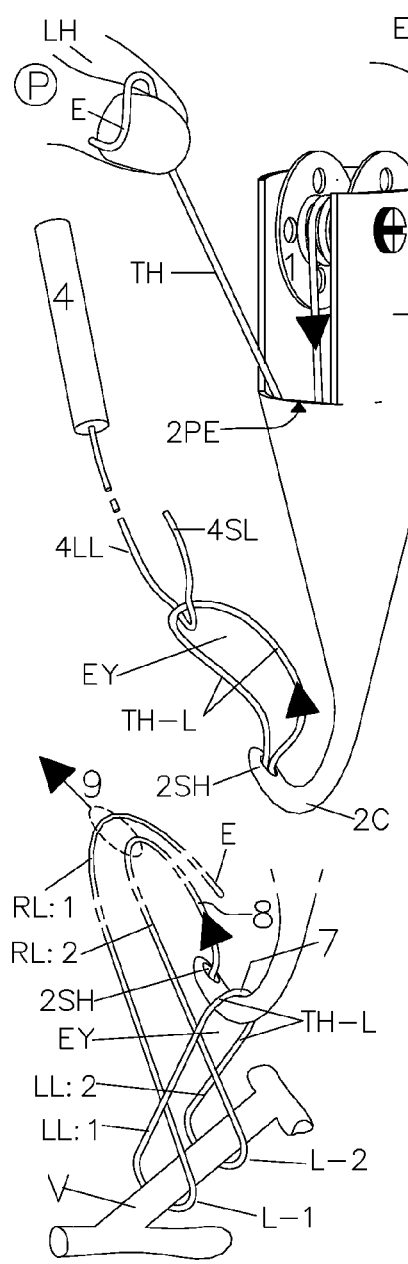
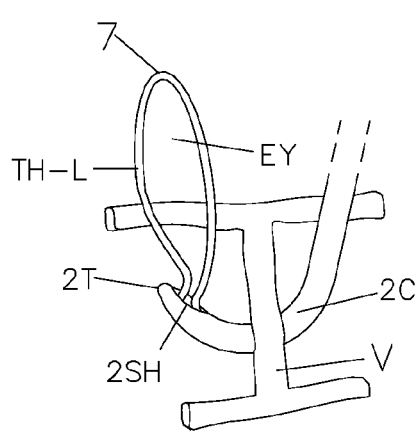
*Fig.6A*
*Fig.6B*
*Fig.6C*
*Fig.6D*

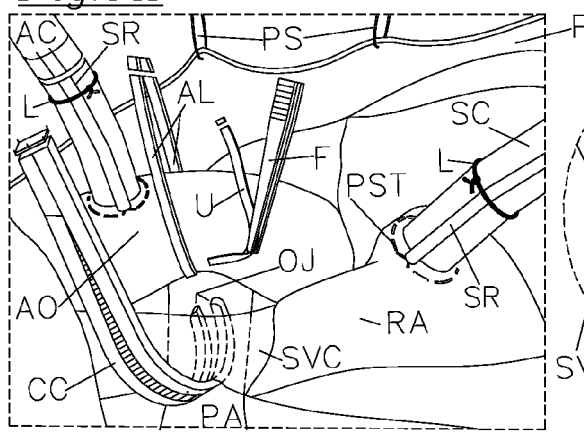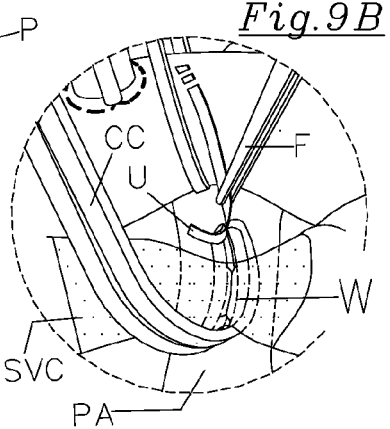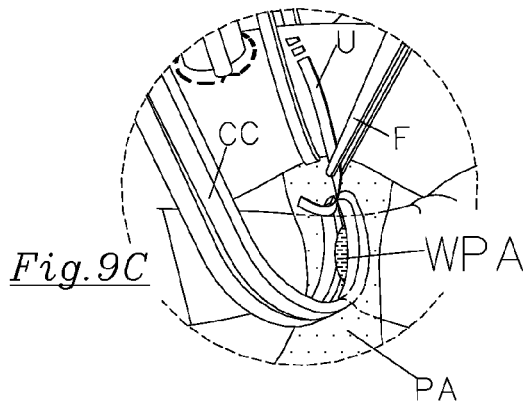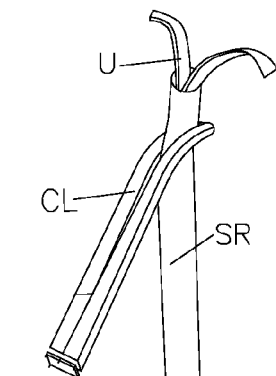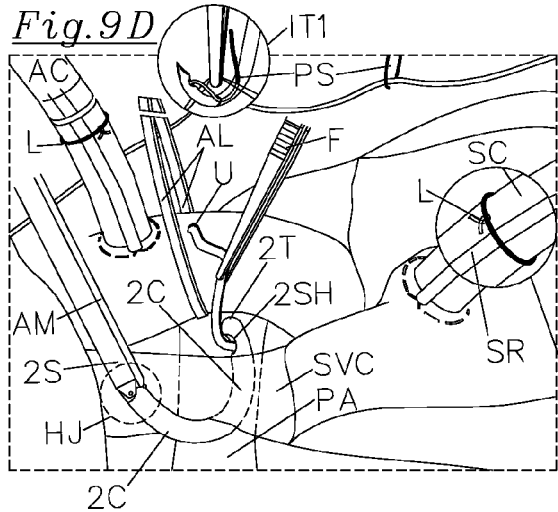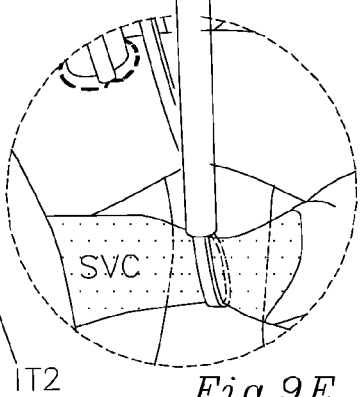

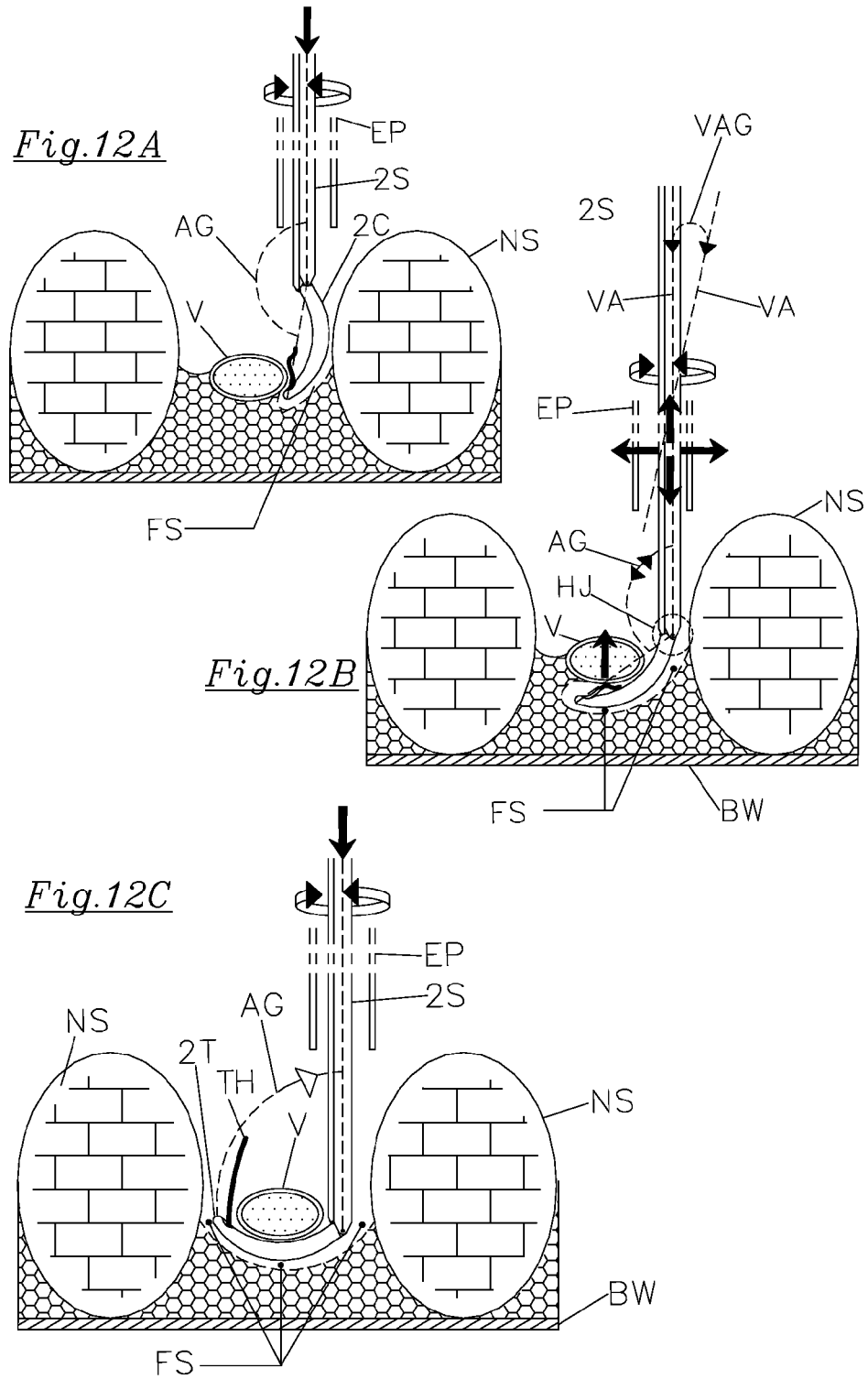

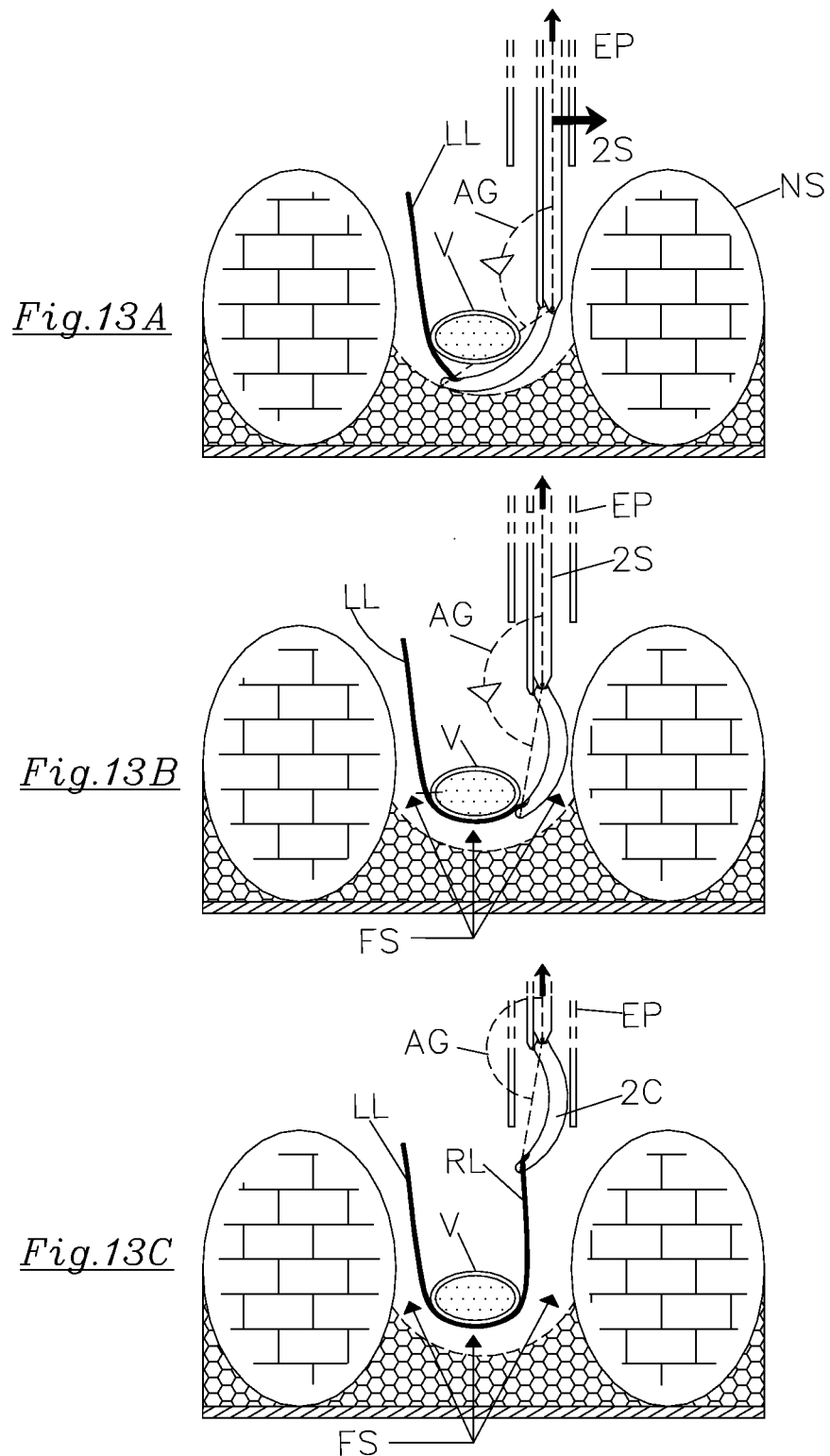

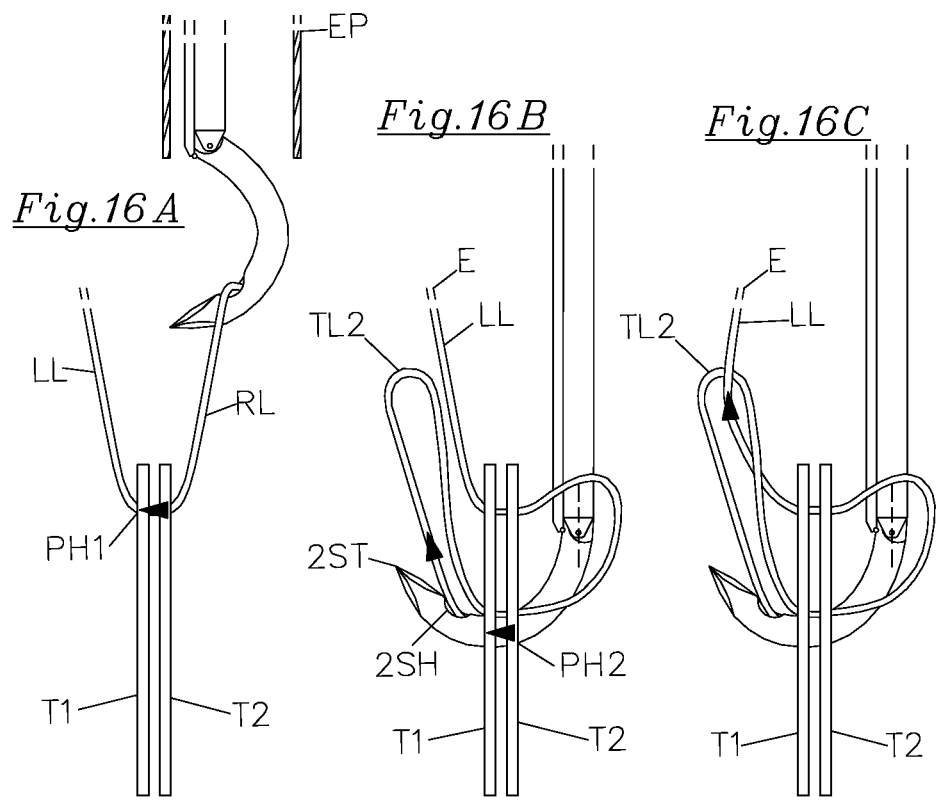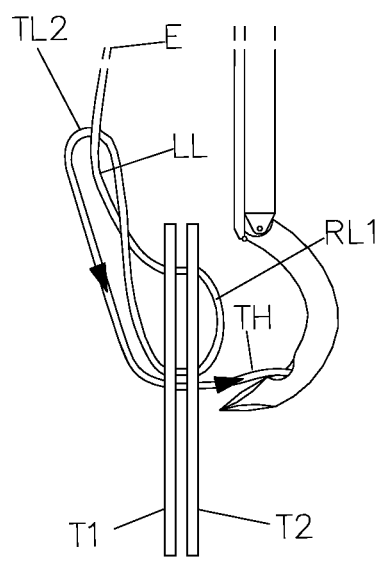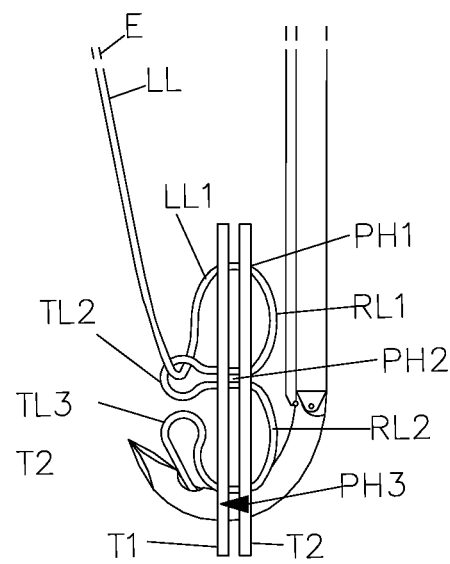

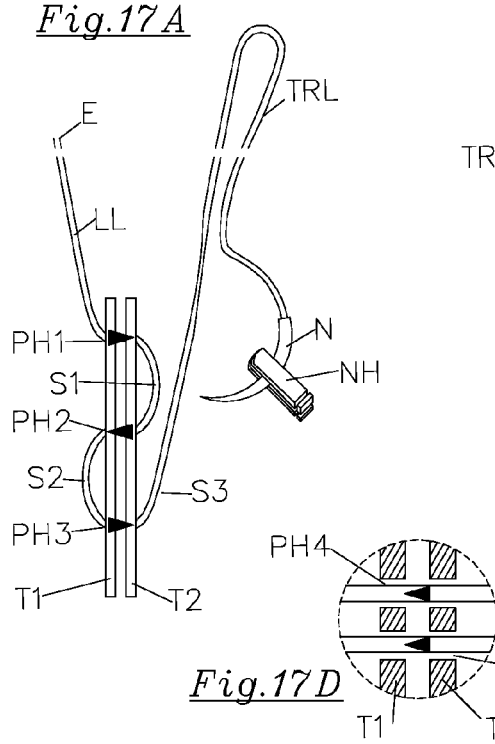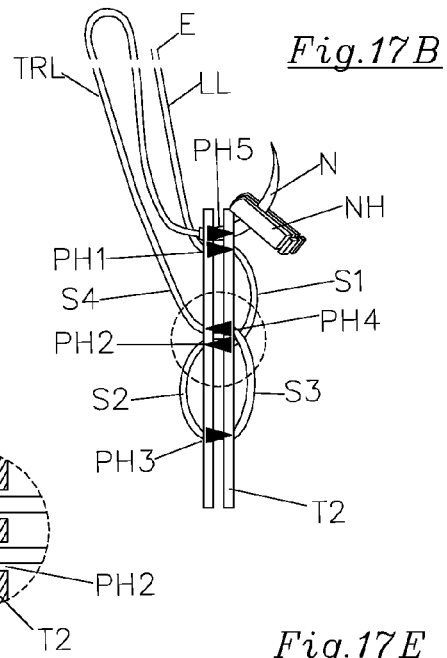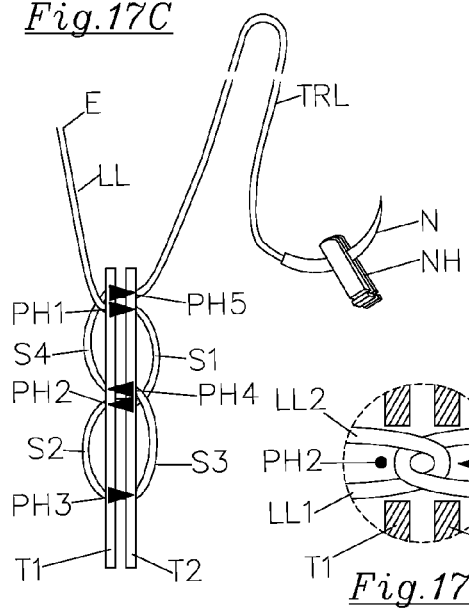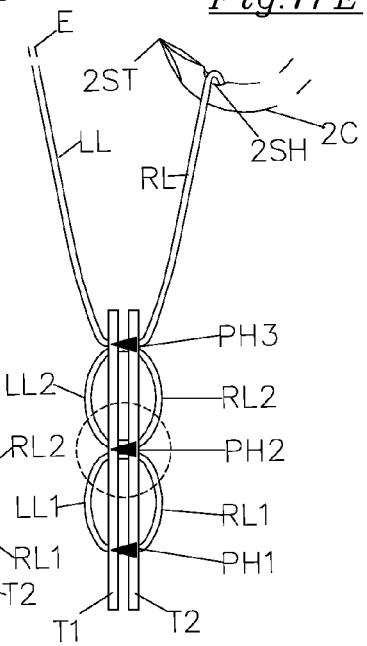
Fig.17A Fig.17B Fig.17C Fig.17D Fig.17E Fig.17F

DEVICE FOR DISPENSING, LOOPING AND TYING LIGATURES

CROSS-REFERENCE TO RELATED APPLICATIONS

This application is a continuation-in-part of PCT Application No. PCT/IN2007/000614, filed Dec. 28, 2007, which claims priority to and the benefit of Indian Application No. 2829/DEL/2006, filed Dec. 29, 2006, each of which is incorporated herein by reference in its entirety.

FIELD OF INVENTION

This invention relates to a device for repetitively dispensing bits of threads or cords for surgical and non-surgical uses and performing surgical ligations employing the novel technique of dispensing, looping and tying ligatures using the device. The device, besides delivering the required length of the suture thread, also helps in passing the dispensed ligature through or around the structure in a single or multiple turns or in the configuration of other known bends and hitches and further helps in tightly securing together the two limbs of the dispensed ligature loop in a knot. The device simplifies this procedure of delivering and tying the ligature loops during endoscopic and robotic surgery.

BACKGROUND OF THE INVENTION

During surgical procedures, bits of suture, i.e. surgical threads or ligatures are used to loop around or pass through body structures. The ligature bit may be passed around the structures in a single turn or multiple turns or in the configuration of other known bends and hitches. These ligatures, for example, are then tied around a blood vessel to constrict it and stop bleeding permanently, pulled to constrict the blood vessel or retract the structure, or tied to bind or hold the parts together. Two ligature bits may be passed alongside to each other looping around the structure and the respective limbs of the ligature tied together and subsequently the structure may be divided in between the tied ligatures. Sutures are made of different materials, thickness and qualities and commercially available either fastened to a needle for sewing tissue, or free of needles. Suture, not attached to needles is mostly used for looping or ligation of structures and is packaged wrapped either on a spool or as bits of predetermined standard length.

Similarly, ligatures or cords are also required in various non-surgical procedures.

It is most important to perform every surgical operation safely without any complications, economically, and speedily as extra time spent during surgery increases the operating cost and endangers the life of the patient.

The Conventional Surgical Technique of Ligation and its Drawbacks

The ligation of a structure for example a vein is done conventionally with the following drawbacks:

1. Bits of surgical suture are procured from commercially available packets or bits of ligature are precut from a reel at the start of the operation by the scrub nurse, going by a rough estimate of the ligature requirement. This wastes time and suture material as the nurse arbitrarily tends to cut long bits of the ligature to suffice diverse purposes. Similarly commercially packaged sutures are of predetermined lengths and are generally longer than required as they are intended to suit diverse purposes.

2. The vein to be ligated is dissected using blunt or sharp instruments and freed from the adjoining structures at the site of ligation creating an adequate space for the subsequent passage of the instruments and the ligature. This wastes time, requires special instruments and is liable to injure the vein and adjoining structures.

3. The surgeon takes a curved or a right-angle surgical clamp and with the jaws closed, the tip of the clamp is passed behind, from one side of the vein, to the extent that the tip is visible on the other side of the vein. The clamp can cause injury to the structures during passage.

4. The jaws of the clamp are opened apart proportional to the thickness of the ligature and the clamp is held in this position. The vein or the adjoining structure may be damaged.

5. One end of the ligature bit held with a forceps by the assistant is positioned within the opened jaws of the clamp. Requires another instrument and assistance.

6. The surgeon to grasp the end of the ligature closes the jaws of the clamp and the clamp is withdrawn back from behind the vein, thus pulling the ligature and forming a 'U' loop around the vein with two equal limbs, on either side of the vein. Before the ligature is pulled around the vein, a suitable fluid is applied to the ligature to decrease the drag on the vein and adjoining structures. Along with the ligature, the wall of the vein or the adjoining structures may be inadvertently caught in the clamp and damaged. The ligature when drawn around the vein is in direct contact with the vein and the adjoining structures and thereby grazes and drags on these structure with a sawing action which requires the ligature to be moistened with a fluid and in spite of the lubrication can still injure the structures.

7. The clamp is removed and the two limbs of the ligature loop are tied in a knot.

8. Proximate to the knot the two limbs of the ligature loop are cut off and discarded. Only a short length of the ligature is actually consumed in the knot, nevertheless, extra length of the suture bit is still required to manipulate and tie the ligature into a knot. Once the knot is tied, the two limbs of the ligature loop are cut off beyond the knot and because of their resultant short lengths—less than half of the original ligature—cannot be used for more ligations and hence discarded. This leads to wastage of expensive sutures.

9. For a more secure ligation, it is often necessary to deploy the same ligature around the vein in more than one turn. To do so requires the repetition of the above-mentioned steps. The clamp is once again passed under the vein in the same direction as in step 3.

10. The end of the ligature limb of the first 'U' loop on the same side of the clamp is crossed over in front and to the opposite side of the vein and grasped in the clamp and is looped around the vein in a second turn by withdrawing back the clamp, as in the abovementioned point 6 eventually looping the same ligature twice around the vein. When grasping and pulling the ligature end a second time not only the vein and the adjoining structure but the first loop of the ligature passing behind the vein may also be grasped and may completely avulse the vein.

11. It is often necessary to divide the vein and this is done by tying two ligatures alongside by repeating the above steps twice and then dividing the vein in between the two ligatures. The ligatures are tied sequentially and not simultaneously, which is time consuming.

12. If the ligature must be passed through a structure than expensive suture with a pre-fastened needle has to be used, or the ligature is passed through an eye needle and used, which is time consuming Moreover, the needle has to be mounted on a needle holder, which requires an additional instrument and more time.

13. It is difficult to perform ligation through the confines of the narrow endoscopic ports during endoscopic surgery, even with the use of endoscopic instruments.

SUMMARY OF THE INVENTION

The present invention relates to a device comprising a cannula with a lumen incorporating a hinge between its proximal end and the distal end and an actuating means for altering the angle at the hinge between the resultant distal segment and proximal segment. Another embodiment of the invention is of the device comprising a cannula having a proximal end, a distal end and a lumen extending in between with the distal end being closed and a side hole communicating with the said lumen preferably proximal to said distal end. The distal end may be in the form of either a blunt tip or sharp tip preferably needle sharp. The device may further comprise a housing to house a spool having cord/ligature wound thereon, said spool mounted in said housing and a lock-unlock mechanism to control dispensing of said cord/ligature.

The present invention preferably relates to a device for dispensing, looping and tying ligature comprising:
- a housing to house the spool having surgical or non surgical thread/cord wound thereon in plurality of turns,
- said spool is mounted rotatably and removably in the housing,
- a cannula mounted to the base of the housing removably and rotatably in its longitudinal axis to carry the thread,
- a lock-unlock mechanism to control dispensing of said thread/cord,
- a snare comprising a steel wire to form a Y shape or hook shape with a narrow pointed tip to thread the said cannula.

Accordingly the invention provides an apparatus comprising of a housing to house the spool having a length of surgical or non surgical thread/cord wound thereon and the said spool is mounted rotatably and removably in the said housing, on an axle spindle or by any other mechanism therein, such that a segment of one or both side guards of the said spool is exposed and uncovered by the said housing and the said uncovered segment of the side guards of the said spool can be touched to manipulate and rotate the spool so as to wind or rewind the thread.

A cannula is either affixed removably and rotatably in its longitudinal axis to the said housing or is composite with the said housing and the proximal end of the said cannula is disposed close to the said spool. The dispensed thread traverses within the cannula without grazing or dragging the adjacent structures. The cannula either comprises of only a straight pipe; or only a curved pipe; or a J shaped pipe with a combination of a proximal straight segment and a distal curved segment; or a combination of a proximal and a distal straight pipe disposed at any desired angle to each other, or the cannula is funnel shaped with a proximal conical segment in continuity with a distal straight or curved cylindrical segment or the distal straight cylindrical segment may be disposed at any desired angle to the proximal conical segment. The said cannula has a distal end hole at the distal tip of the cannula, or the said distal end hole is closed off, and the distal tip of the said cannula is rounded into a blunt shape and a side hole communicating with the lumen of the cannula is made proximal to the said closed-off distal tip for the passage of the thread and the snare. In another embodiment the distal end hole at the distal tip of the cannula, is closed off, and the distal tip of the said cannula is honed in the configuration of a surgical needle and a side hole communicating with the lumen of the cannula is made proximal to the said closed-off and honed distal tip for the passage of the thread and the snare, and the said cannula is used to pierce the structure and dispense the ligature passing through the structure. In another embodiment a hinge joint is incorporated between the proximal segment and the distal segment of the cannula that permits angular movement of the distal segment controlled manually by an incorporated actuating mechanism and the said 'swivelable cannula' is used for looping the structures and also to negotiate the said 'swivelable cannula' in its narrow straightened or folded configuration across the endoscopic ports into the body cavity during endoscopic surgery.

A 'lock-unlock' mechanism to restrain the dispensing of the thread from the device, comprising of an exposed segment of one or both side guards of the said spool, that is uncovered by the said housing and can be touched to stop the unwinding of the said spool, may be designed at the top, front, back or the sides of the said housing or at multiple locations, or may also be designed in the form of any manually activated mechanical or electro-mechanical mechanism incorporated in the embodiment which may act either on the spool or the thread or both spool and the thread.

A snare comprising a fine steel wire bent in the shape of 'Y' or a 'hook', to form a narrow tip is used to thread the said cannula. The fine tip of the snare wire loop is introduced into the distal hole (side-hole or end-hole) of the cannula and the snare is pushed up till it emerges out of the proximal end-hole of the cannula and forms a small loop of wire thereon, in the vicinity of the spool, into which the free end of the thread wrapped on the spool is passed. The snare is then completely withdrawn out of the cannula, which traps the free end of the thread and delivers it out of the distal hole of the cannula thus threading the cannula. The excess length of the thread that emerges out of the cannula is wound back on the spool by manually rotating the spool by the uncovered segments of its side guards. When threading the cannula for specific purposes a loop of thread rather than just the free end of the suture is brought out from the distal hole of the threaded cannula Dispensing of the ligature to ligate a vein: The invention 'device for dispensing, looping and tying ligatures' is used in the following manner to dispense a ligature looping around a vein and then tying the two limbs of the dispensed ligature loop in a knot eventually ligating the vein. The distal tip of the threaded 'J' shaped cannula, which has a short length of the threaded suture emerging out of the distal side-hole, is passed behind and across from say the right side to the left side of the vein to the extent that the suture thread emerging out of the distal side-hole of the cannula becomes visible on the left side of the vein. The device is held in this position and the spool is permitted to rotate freely (the thread is 'unlocked') the suture thread emerging out of the distal side-hole at the distal tip of the cannula is grasped and pulled to unwind the suture thread from the spool and eventually withdraw the required length of the left limb of the U loop on the left side. While still holding the free end of the thread on the left side of the vein, the distal tip of the cannula is withdrawn back completely to the right side of the vein; and the invention device is moved away from the vein till the required length of the right limb of the U loop on the right side of the vein is dispensed thus completing the U loop of thread around the vein. Further unwinding of the thread from the spool is prevented by touching the side guards of the spool (thus 'locking' the thread) the two limbs of the U loop, (left being held in the left hand and the right emerging out of the tip of the cannula of the invention device which is being held in the right hand), are gently pulled and manipulated to tie a secure knot thus ligating the vein. The two limbs of the ligature are cut proximate the knot and the severed left limb of the ligature is discarded. The remnant of the right limb of the ligature loop still continuous with the suture thread on the spool is saved and is rewound on to the spool by manipulating the uncovered segments of the side guards of the spool, leaving only a short segment emerging out of the distal side hole of the cannula. By using the invention device and the novel technique of dispensing, loping and tying ligatures, the ligature is dispensed traversing within the lumen of the said cannula neither grazing or dragging the structure being looped nor grazing or dragging any adjacent structure.

Employing the novel technique of dispensing, looping and tying ligatures by using only one device single ligatures are dispensed, one at a time, looping around the structure in a single-loop or a double-loop, or even two ligatures can be dispensed alongside looping around the structure, and eventually the limbs of the dispensed ligature may be tied together if required.

By using two devices and a snare in cooperation ligatures are dispensed looping around a structure in multiple loops or in the configuration of known bends and hitches, and eventually the limbs of the dispensed ligature may be tied together if required.

Further objectives and advantages of the present invention 'device for dispensing, looping and tying ligatures' will become evident herein below by a consideration of a detailed description of specific exemplary embodiments thereof with reference to the accompanying drawings illustrated on a total of sixteen drawings sheets numbered serially 1 to 16.

BRIEF DESCRIPTION OF THE DRAWINGS

FIG. 1A is the front elevational view of the device.

FIG. 1B is an elevational side profile of the device as viewed from the right side of FIG. 1A.

FIG. 1C is an enlarged, perspective view of the device.

FIG. 1D is an enlarged, front cross-section view taken on line 12-12 of FIG. 1B.

FIG. 1E is the perspective view of the construction details of the spool 1.

FIG. 2A is an elevational view illustrating one embodiment of the snare 4.

FIG. 2B is an enlarged, elevational, front view of the device illustrating the manner in which the wire loop snare 4 is inserted in the cannula 2 in order to snare the thread TH.

FIG. 2C is an elevational, front view of the device with the cannula 2 having been threaded with the thread TH from the spool 1.

FIG. 3A is a perspective view showing the left limb LL of the loop L being dispensed.

FIG. 3B is a perspective view illustrating the right limb RL of the loop L being dispensed.

FIG. 5A is a perspective view of the terminal portion of a 'J' shaped 'swivelable-cannula', incorporating a hinge joint mechanism HJ at the junction of the distal curved segment 2C with the proximal straight segment 2S, in its narrow 'straightened configuration' while passing through an endoscopic port EP shown in a longitudinal section.

FIG. 5B is a magnified view of the terminal portion of a 'swivelable-cannula', as in FIG. 5A, which has been swiveled into the curved configuration after it has emerged out of the distal end DE of the endoscopic port EP illustrated in a longitudinal section.

FIG. 5C is a magnified view of the terminal portion of a cannula with a honed distal tip 2ST and the suture end E emerging out of the side hole 2SH.

FIG. 6A is a perspective view of an embodiment of the device with the housing, represented by the two side arms 3RA and 3LA, being composite with a 'funnel shaped' cannula 2F and the cannula is being threaded with the thread TH on the spool 1 by employing the 'hook shaped' snare 4 while the left hand LH holds the end E of the thread TH.

FIG. 6B is a perspective view illustrating the threaded device as in FIG. 6A with the 'hook shaped' snare 4 withdrawn out of the side hole 2SH delivering a thread loop TH-L.

FIG. 6C is a perspective view illustrating the distal curved segment 2C of the cannula having passed behind the vein V, with the thread loop TH-L emerging out of the side hole 2SH on the left side of the vein V.

FIG. 6D is a perspective view illustrating the dispensing of two loops L-1 and L-2 around the vein V in the configuration of a 'cow hitch'.

FIG. 8A depicts the cannula as in FIG. 5A but with the needle sharp tip 2ST and its usage is further elaborated in FIGS. 14 A-F, 15 A-F and 16A-E.

FIG. 9A depicts a typical scenario of cardiac surgery employing cardio pulmonary bypass and the Superior Venae Cava SVC is being looped with an umbilical tape U using the conventional curved clamp CC.

FIG. 9B depicts the back wall W of the Superior Venae Cava SVC grasped by the curved clamp CC.

FIG. 9C depicts the front wall WPA of the Pulmonary Artery PA grasped by the curved clamp CC.

FIG. 9D depicts a typical scenario of cardiac surgery as in FIG. 9A, and shows the Superior Venae Cava SVC being looped with an umbilical tape U using the invention device. Insert IT1 depicts the passage of pericardial stay sutures PS using the invention device and insert IT2 depicts the ligature LL tied around the snare SR and the Superior Venae Cava cannula SC.

FIG. 9E depicts the vascular tourniquet in place snaring the Superior Venae Cava SVC.

FIG. 12A depicts the free space FS being created on the right side of the vein V using the invention device.

FIG. 12B depicts the reduced angle AG and the free space FS being created below the vein V. The possible movements of the invention device utilized for blunt dissection are depicted by the corresponding arrows.

FIG. 12C depicts the reduced angle AG and the free space FS being created on the left side of vein V.

FIG. 13A depicts the dispensed left limb LL, the curved segment 2C withdrawn behind the vein V and the increased angle AG.

FIG. 13B depicts the curved segment 2C withdrawn to the right side of the vein V and the increased angle AG.

FIG. 13C depicts the dispensed limbs LL and RL of the ligature, looped around the vein V and positioned in the free space FS created by the invention device which is being withdrawn out of the endoscopic port EP.

FIG. 16A diagrammatically depicts the already deployed first loop, with left limb LL and right limb RL, passed through the puncture hole PH1 in the tissues T1 and T2, located within the body cavity, to be sutured by the technique of 'continuous through and through suturing' using the device through the endoscopic port EP.

FIG. 16B depicts the tip 2ST passed through the second puncture hole PH2 in the two tissues T1 and T2 and the thread loop TL2 is being enlarged.

FIG. 16C depicts the ligature end E of the left limb LL passed through the ligature loop TL2.

FIG. 16D depicts the withdrawn tip 2ST and the ligature TH is being withdrawn to reduce the ligature loop TL2.

FIG. 16E depicts the reduced ligature loop TL2 and the deployed suture segments LL1 and RL1. The tip 2ST has pierced the two tissues T1 and T2 through the third puncture hole PH3 beneath the second puncture hole PH2 and the thread loop TL3 is visible on the left side of tissue T1.

FIG. 17A depicts 'continuous through and through suturing' of two tissues T1 and T2 during an open procedure using the conventional needle N (with the swaged ligature) and the needle holder NH. The ligature has been passed through the puncture holes PH1, PH2 and PH3 and the needle is held in the forehand grip with the needle holder NH in preparation of piercing the tissues again through the fourth puncture hole.

FIG. 17B depicts the needle N held by the needleholder NH in the backhand grip, being withdrawn out of the fifth puncture hole PH5 in tissue T1 and T2.

FIG. 17C depicts the completed suture line using the swaged needle N and the needle holder NH.

FIG. 17D depicts a magnified longitudinal section view through the encircled region in FIG. 17B

FIG. 17E depicts the completed 'continuous through and through suture' line using the invention device.

FIG. 17F depicts a magnified longitudinal section view through the encircled region in FIG. 17E

BRIEF DESCRIPTION OF THE DRAWINGS

The Constructional Details of the Device

Figure 4A:
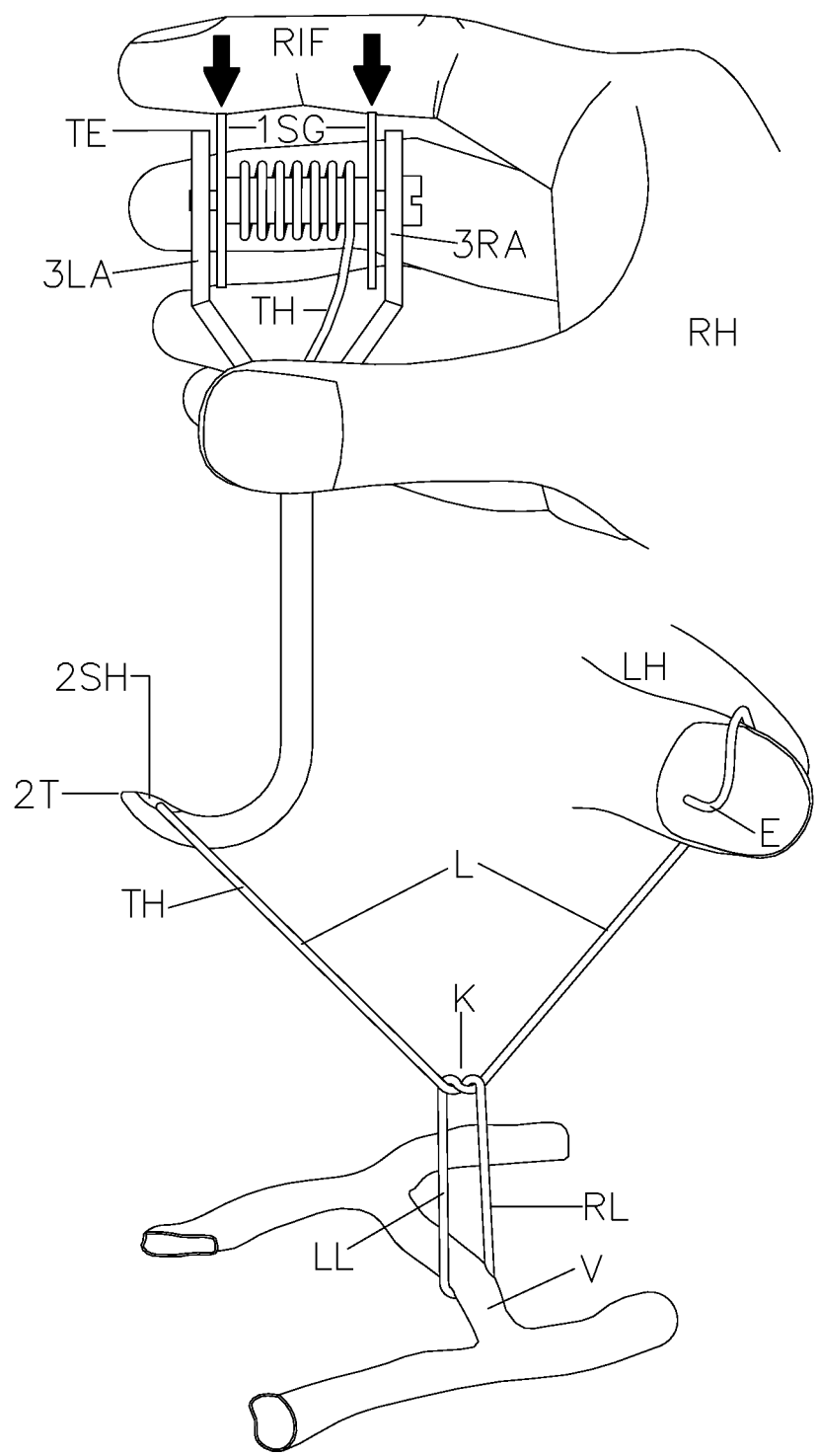
FIG. 4A is a perspective view showing the manner in which the two limbs LL and RL of the U loop L are being tied into a knot K.

The Spool 1: The constructional features of the spool 1 are demonstrated in FIG. 1E on drawing sheet No. 1. The spool 1 has a central cylindrical hub 1CS having an axial opening 1CH therein and side guards 1SG of equal or unequal diameter on either side of the said hub 1CS which in cooperation of each other and said hub 1CS form an annular channel adapted to carry a length of surgical or non-surgical thread TH or a cord wound thereon. Multiple holes 1MH spaced and sized appropriately are made in the central cylindrical hub 1CS and the two side guards 1SG. These holes 1MH serve to decrease the mass of the spool 1 and hence decrease its inertia and also allow permeation of steam or other sterilization agent deeper into the coil of the suture thread TH wound in the spool 1.

An axel spindle AS in the shape of a screw or bolt with threads at the terminal end TT passes through the axial opening 1CH within the hub 1CS of the spool 1, the outside diameter of said spindle AS being sized to receive the axial opening 1CH in said hub 1CS to allow the spool 1 to rotate freely in either direction on said axel spindle AS, and the axel screw AS mounts the spool 1 removably within the housing 3, as illustrated in the FIGS. 1A, 1D and 6A. Instead of mounting the spool 1 on an axel spindle AS, as illustrated in the FIGS. 1A, 1D and 6A, the spool 1 may also be mounted rotatably and removably within the housing 3 employing other mechanisms. The spool 1 is made up of a nontoxic metal or alloy or a plastic that can withstand the sterilization process and is preferably made in a single piece that eliminates any joint space, into which dirt and microbes can accumulate. The spool is constructed in a scale that will hold sufficient suture for the intended task.

The Housing 3: The housing may be made from a metal, alloy or plastic. In the exemplary embodiment as depicted in the FIGS. 1A, 1B, 1C, and 1D the housing is made in the shape of letter 'U' with two parallel facing side-arms 3RA and 3LA that continue downward to converge and taper symmetrically as the respective oblique segments 3R0 and 3L0 that finally fuse to a central base 3B. A hole 3BH is made in the longitudinal axis passing through the central base 3B of the housing 3, and the diameter of the said central hole 3BH is sized to receive the proximal end 2PE of the cannula 2 as depicted in FIGS. 1A and 1D. The central base 3B of the housing 3 has another internally threaded hole FSH that is disposed at right angle and in alignment to the said central hole 3BH, that receives the proximal end 2PE of the cannula 2, and into the said threaded hole FSH a fixing screw FS is screwed in that removably and rotatably holds the cannula 2 to the central base 3B of the housing 3, as depicted in FIGS. 1A and 1D. This mechanism of fixing the proximal end 2PE of the cannula 2 removably and rotatably, by the fixing screw FS in the hole 3BH of the housing 3, permits 360 rotation of the cannula in its longitudinal axis and thereby the curved segment 2C of the cannula 2 can be made to point in the required direction relative to the orientation of the housing 3; and also minor adjustment of the cannula length emerging out of the housing can be made. The cannula 2 may be fixed by other suitable mechanisms also that permit rapid and easy exchange of the cannulae; permit adjustment in the cannula length emerging out of the housing; allow adjustment in the orientation of the curved cannula tip 2T in the longitudinal axis.

The axle spindle AS passes transversely, through two aligned and sized holes ASH-R and ASH-L in the two said parallel facing side-arms 3RA and 3LA, respectively, of the housing 3 and the said hole ASH-L in the left side-arm 3LA is internally threaded into which the threaded end TT of the axle spindle AS is screwed in as illustrated in FIGS. 1A and 1D. The two said parallel facing side-arms 3RA and 3LA of the housing 3 are disposed at a distance sufficient enough to permit the spool 1 to be mounted on the axle spindle AS rotatably within the confines of the two side-arms 3RA and 3LA. The spool 1 may be easily removed from the housing 3 by unscrewing and removing the axel spindle AS. The dimensions of the two side-arms 3RA and 3LA of the housing and the placement of the axle spindle AS thereon are such that the two side-arms 3RA and 3LA of the housing 3 extends radially beyond and cover the side guards 1SG of the mounted spool 1, preventing the accidentally touching of the side guards 1SG of the mounted spool 1 which would hamper the rotation of the spool 1; except in one region at the top of the housing 3 where one or both side guards 1SG of the spool 1 project a little beyond the corresponding top edge TE of one or both side-arms 3RA and 3LA of the said housing 3, and this uncovered segment of one or both side guards 1SG of the spool 1 can be intentionally touched to stop the rotation of the spool when required, as illustrated in the FIGS. 1A, 1B, 1C, 1D, 4A, 6A and 6B.

This said region where the segments of the side guards 1SG of the spool 1 are uncovered and project beyond the limits of the two side-arms 3RA and 3LA of the housing 3 can be designed either at the top as illustrated in the FIGS. 1A, 1B, 1C, 1D, 4A, 6A and 6B and also in the front or the back of the housing but preferably at the top that will permit the housing 3 to be held or placed on a table in the front-back or side-side orientation without hampering the rotation of the spool 1.

The spool 1 mounted on the axle spindle AS within the housing 3 can be manually rotated by manipulating these uncovered segments of the side guards 1SG of the spool 1, in order to wind and load suture thread TH on the spool 1 or to rewind the extra length of the suture thread unwound from the spool as illustrated in the FIGS. 3A and 4A. The spool 1 can also passively rotate within the housing 3 and unwind the loaded suture thread TH wrapped on the spool 1 when the suture TH is pulled and dispensed as illustrated in FIGS. 2C, 3A and 6B. The rotation of the spool 1 can be halted or prevented by touching and pressing, as illustrated in the FIG. 4A, with the right index finger RIF of the right hand RH holding the device, on the uncovered segments of the side guards 1SG of the spool 1 that project beyond the top edge TE of the two side arms 3RA and 3LA. Stopping the rotation of the spool 1 thus, stops the unwinding of the spool and the subsequent release of the thread TH, or in other words the thread can be 'locked' in by touching and pressing the uncovered segments of the side guards 1SG of the spool 1 as illustrated in the FIG. 4A. Permitting the spool 1 to rotate, by removing the finger RIF away from the side guards 1SG of the spool 1 as illustrated in FIG. 3A, 'unlocks' the thread TH in other words allows the unwinding and dispensing of the thread TH when the thread TH is pulled as illustrated in FIGS. 2C, 3A and 6B. 'Locking' the thread prevents the release of the thread TH from the spool 1 thus builds up the required tension in the two limbs RL and LL of the dispensed U-shaped ligature loop L that is necessary to fasten a secure knot K can be generated as illustrated in FIG. 4A. 'Locking' of the thread, as achieved by manually pressing on the side guards 1SG of the spool 1 thereby halting and preventing the rotation of the spool 1 as illustrated in the exemplary embodiment, may also be achieved by many other mechanical or electro-mechanical mechanisms deployed on the housing 3 or the spool 1 or on both housing and the spool which may be in the form of a friction pad, lever, spring or an electromagnet that can be actuated manually. These 'locking mechanisms' may be designed to either act on the spool 1 as in this exemplary embodiment illustrated in FIG. 4A, or even act directly on the thread TH per se or act on both the spool and the thread. These 'lock-unlock mechanism' may be so designed that the 'thread is unlocked' i.e. free to be dispensed all the time and actively 'locked', thus preventing the release of the thread, only when needed and desired as in this exemplary embodiment illustrated in FIG. 4A or in the opposite configuration of the thread being 'locked' all the time and actively 'unlocked' only when needed and desired.

In this exemplary embodiment the front and the back of the housing 3 is purposely left uncovered which permits the visualization of the mounted spool 1 with the loaded thread TH thereon, the end of the loaded thread E, the tip 4T and wire loop 4WL of the wire loop snare 4 emerging out of the proximal hole 2PH at the proximal end 2PE of the cannula 2, as illustrated in FIGS. 2B and 6A. This visualization is essential for the end E of the suture thread TH to be picked and passed through the wire loop 4WL and the subsequent threading of the cannula 2 with the suture thread TH. Other embodiments may be designed in which once the cannula is threaded, as described in detail later, the said front and the back of the housing 3 may be covered appropriately, that will prevent—the soiling of the loaded suture thread TH, unintentional touching of the side guards 1SG and thereby impeding the rotation of the spool 1 and also make the housing more ergonomic to hold.

The Cannula 2:

The said cannula 2 comprising a metallic or plastic pipe with a proximal end 2PE and a proximal end-hole 2PH and a distal end 2T and a distal hole 2SH; and the proximal end 2PE is disposed close to the spool 1 being affixed to the central base 3B of the housing 3 by the fixing screw FS as described earlier. In exemplary embodiment the cannula 2 is made in the configuration comprising a combination of a proximal cylindrical straight segment 2S that continues as a distal tubular curved segment 2C resembling the letter 'J'. The cannula may be also made in several other configuration either comprises of only a straight pipe; or only a curved pipe; or a combination of a proximal and a distal straight pipe disposed at any desired angle to each other, or the cannula may be made funnel shaped with a proximal conical segment in continuity with a distal straight or curved cylindrical segment or the distal straight cylindrical segment may be disposed at any desired angle to the proximal conical segment. When the cannula 2 is made of a thin walled pipe which is necessary in order to restrict the external diameter of the cannula 2 and also have the largest possible internal diameter, and is needed for dispensing fine suture threads for looping friable and fine body structures, then the edges of the cannula 2 at the distal end-hole if made right at the distal tip 2T and also the proximal end-hole 2PH can become very sharp which can fray and damage the ligature during its movement through the cannula 2. This sharp edge of a thin walled cannula 2 having the distal hole at the distal tip 2T can also damage the body parts when the distal tip 2T of the cannula 2 is negotiated around the body structure. To overcome this problem of damage to the suture thread by the sharp edges of the proximal end-hole 2PH the proximal end 2PE of the cannula 2 is made of a thicker-walled pipe and the proximal edge of the cannula around the proximal end-hole 2PH is smoothly rounded to prevent fraying of the ligature thread TH entering the cannula 2 as illustrated in the FIG. 1D; and the proximal end 2PE or the entire cannula 2 can be made 'funnel-shaped' or 'conical' as illustrated by the 'funnel shaped' cannula 2F in the FIGS. 6A and 6B, and the 'funnel shaped' cannula 22 in FIG. 7C which would minimize the chances of the suture thread brushing against the edge of the proximal end 2PE of the cannula and also facilitate in threading of the cannula with the snare as described later. To reduce the chances of injury to the body parts during ligation, the end hole at the distal tip 2T of the cannula 2 is closed off and the tip 2T smoothly rounded into a non-traumatic blunt shape and for the suture thread and the snare to emerge out of the distal end of the cannula 2 an elliptical side hole 2SH, of sufficient diameter, in communication with the cannula lumen, is made proximal to the closed off blunt distal tip 2T. This distal elliptical side hole 2SH may be placed proximal to the closed off blunt distal tip 2T anywhere on the entire circumference of a cannula 2 that comprises of only a cylindrical straight segment 2S, but preferably located on the inside curve if the distal segment of the cannula 2 is curved because the suture thread TH emerging out of the side hole 2SH on the inner curve is clearly visible when looking from the top, and is easily pulled. The cul-de-sac CDS distal to the side hole 2SH extending internally to the closed off tip 2T of the cannula 2 is obliterated to allow smooth entry and exit of the suture thread TH and the snare 4 through the distal side hole 2SH as illustrated in FIG. 1D.

The proximal end 2PE of the cannula 2 may be irremovably, but preferably removably fixed in the housing, as aforementioned in the exemplary embodiment illustrated in FIGS. 1A, 1B, 1C, and 1D, with a fixing screw FS or any other suitable mechanism may be employed that permits rapid and easy exchange of the cannulae; permits adjustment in the cannula length emerging out of the central base 3B of the housing 3; allows adjustment in the orientation of the curved segment 2c in the longitudinal axis relative to the orientation of the housing.

In another embodiment illustrated in FIGS. 6A and 6B the cannula 2 represented by the proximal segments 2F and the distal curved segment 2C and the housing represented by the two side arms 3RA and 3LA are constructed or molded as a single composite embodiment. The cannula 2 is 'funnel' shaped with a distal tubular curved segment 2C that continues proximally as the conical segment 2F which after attaining the maximum diameter at the top proximal end 2PE continues as the two side arms 3RA and 3LA of the housing. The two side arms 3RA and 3LA of the housing are opposing segments of a straight cylinder that continues superiorly from the top proximal edge 2PE of the funnel shaped cannula 2F. The relative dimensions of the side arms 3RA and 3LA, the diameter of the two side guards 1SG of the spool 1 and the placement of the axel screw AS with the mounted spool 1 on the two arms 3RA and 3LA within the housing and the projection of the uncovered segments of the side guards 1SG beyond the top edge TE of the two arms 3RA and 3LA of the housing and the closure of the distal tip 2T of the curved segment 2C of the cannula 2 with the creation of the side hole 2SH follow the same principle as delineated in the aforementioned embodiment illustrated in FIGS. 1A to 1D, FIGS. 3A and 4A.

The lumen 2L in other words the internal diameter of the cannula and the diameter of the proximal and distal holes 2PE and 2SH respectively of the cannula determine the thickness of the suture thread TH that can be threaded in the cannula 2 and subsequently dispensed by any particular invention device. Depending upon the thickness of the suture thread to be dispensed, an invention device is chosen accordingly, which has a cannula 2 with an internal diameter of the lumen and the diameter of the proximal and distal holes 2PE and 2SH respectively at least two and half times or greater than the diameter of the suture thread to be dispensed (as two diameters of the suture thread TH plus two diameters of the wire loop snare wire have to pass simultaneously while threading the cannula 2 using a wire loop snare 4). To minimize the chances of injury to the structure being ligated an invention device with the finest size cannula 2 that can dispense the required suture thread TH should be used. The length of the cannula depends upon the working distance or the depth of the structure to be ligated. When looping a tubular structure, the diameter of the tubular structure determines the radius of curvature and the length of the arc of the distal curved segment of the T shaped cannula that must be used. Very large tubular structures can be easily looped with the ligature by using a device with a cannula having a distal curved segment 2C with proportionally a longer radius of curvature and a longer length of the arc. However the length of the arc of the distal curved segment 2C of the cannula 2 is preferably kept less than half the circumference of the circle of which the arc is as part of, because a curved segment 2C of the cannula 2 that is longer than half the circumference of the circle will be difficult to negotiate around the tubular structure being looped. This also implies that for different tasks accordingly various cannulae with different lengths, curvature and length of the distal curved segment, different internal and external diameter and the diameter of the proximal and distal end-holes or distal side-hole of the cannula are required. For this purpose it is convenient to incorporate a fixing mechanism that removably fixes the proximal end 2PE of the cannula to the central base 3B of the housing 3 and permits easy and rapid exchange of different size cannulae.

During endoscopic surgery as illustrated in FIGS. 5A and 5B, the endoscopic ports EP have small internal diameters and lumens which restricts the size of the curved segment 2C of the cannula 2 that can be passed into the body cavity through the endoscopic ports EP that ultimately limits the size (diameter) of the tubular structures that can be looped endoscopically. To overcome this problem another embodiment of the invention device comprising of a 'J' shaped 'swiveleable-cannula' incorporating a hinge joint HJ mechanism at the junction of the distal curved segment 2C with the proximal straight segment 2S is used as illustrated in FIGS. 5A and 5B. The radius of curvature and the length of the arc of the distal curved segment 2C are kept conveniently as large as necessary depending upon the diameter of the internal structure to be looped and the cannula 2 is straightened (or folded) at the hinge joint HJ which reduces its effective lateral dimension or extent, when negotiating it through the endoscopic port EP as illustrated in FIG. 5A. Once the straightened (or the folded) distal curved segment 2C of the cannula 2 exits the endoscopic port EP and enters in the more capacious body cavity the cannula 2 is reverted to its more curved configuration as illustrated in FIG. 5B which restores its effective lateral dimension or extent thereby enabling the looping of large diameter tubular structures endoscopically. When beginning to negotiate the curved segment 2C of the 'swivelable-cannula' around a tubular structure during endoscopic or non-endoscopic ligation, the distal curved segment 2C is kept in a less curved and straighter configuration as the tip 2T of the cannula 2 has to pass almost vertically down along the ipsilateral side of the tubular structure; as the tip 2T of the cannula 2 gradually reaches the back of the tubular structure the configuration or the angulation of the distal curved segment 2C of the cannula 2 at the hinge joint HJ with the proximal straight segment 2S of the cannula 2 is gradually and accordingly made 'more curved', and finally when the cannula tip 2T has been negotiated to the contra-lateral side of the tubular structure and begins to ascend, the configuration or the angulation of the distal curved segment 2C of the cannula 2 at the hinge joint HJ with the proximal straight segment 2S of the cannula 2 is made even more curved so that the tip 2T of the cannula 2 and the side hole 2SH on the distal curved segment 2C of the cannula 2 through which the suture end E emerges out is easily visible. This embodiment of the 'swivelable cannula', as illustrated in FIGS. 5A and 5B, permitting manually controlled angular movement of the distal curved segment 2C at the incorporated hinge joint HJ in the cannula 2 is helpful for negotiation of the cannula 2 through the narrow endoscopic ports EP and also simplifies the negotiation of the curved segment 2C around the tubular structure for both endoscopic and non endoscopic ligation as the tip 2T of the cannula 2 can be made to glide along matching the curvature and contour of the tubular structure being ligated thereby minimizing the chances of injury. The angular movement of the distal curved segment 2C at the incorporated hinge joint HJ mechanism in the cannula 2 is achieved and precisely controlled manually by an incorporated 'single action jaw' actuating mechanism AM made in the 'pistol type', 'plunger type' or similar configuration analogous to the one used in endoscopic instruments of prior art.

Another embodiment of the invention device is used to loop the dispensed suture thread piercing and passing through a tissue or structure rather than around it: In this situation the distal tip 2ST and the distal part of curved (or straight) segment 2C of the cannula 2 is honed into a sharp needle-point 2ST and shaped in the various known configurations of surgical needles so that it may easily penetrate into the structure and a side-hole 2SH is made, a little distance proximal to the honed tip 2ST, for the suture end E (and the snare 4) to emerge out of the cannula 2, as illustrated in FIG. 5C. When honed into a needle-shaped point the tip 2ST of the cannula end even the entire cannula 2 is made of a surgical needle-grade alloy.

Figure 7A:
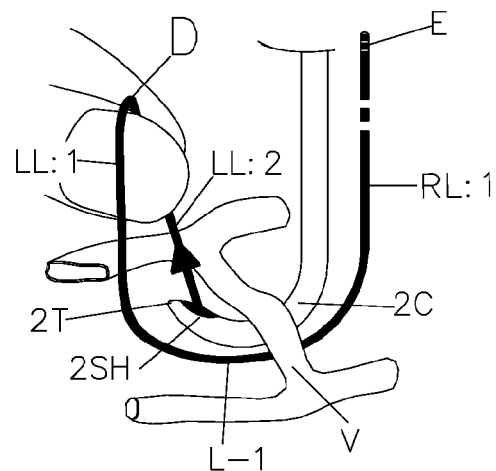
FIG. 7A is a perspective view to illustrate two left limbs LL:1 and LL:2 being dispensed at the same time around the vein V.

Another embodiment of the cannula without the incorporated or attached housing and the mounted spool is used in conjunction with a snare for the sole purpose of snaring and retrieving suture threads: The cannula 22, as illustrated in the FIG. 7C, is made in the shape of a 'funnel' comprising a distal curved segment 2C with a side hole 2SH on the inner curve proximal to the distal closed and blunt tip 2T and has been positioned behind a vein V, passing from the left side of the vein to its right side, that has already been looped once with a ligature loop LL and RL using the invention device; the snare 4 is passed in through the wider proximal hole 2PH on the proximal end 2PE and emerges out of the distal side hole 2SH forming a small loop 4WL thereupon through which the end E of the shown left limb LL of the already dispensed ligature is threaded. The wire snare 4 is subsequently completely withdrawn out of the proximal hole 2PH of the cannula 22 which snares the suture end E and threads the left limb LL of the ligature loop into the cannula 22. The cannula 22 is subsequently withdrawn to the left side and then away from the vein V to deliver out of the left limb LL of the ligature loop that has thus completed the second turn around the vein V finally deploying a double loop DL around the vein V. The larger proximal end 2PE of the cannula 22 shaped like a funnel and the resultant large proximal hole 2PH make the cannula more ergonomic to hold and allows easy insertion of the snare 4 into the cannula 22. The cannula 22 in combination with the snare 4 can be used in the manner described to independently loop ligatures around different structures and if the tip 2T is honed in the aforementioned manner the cannula 22 and the snare 4 combination can be used to pass ligatures penetrating through the structure functioning like a bradawl. This combination of the cannula 22 and the snare 4 can be also used in conjunction with the invention device having the mounted loaded spool to form varieties of loops, bights, knots and hitches as illustrated in FIG. 7C where a double loop DL is being deployed around the vein V.

The wire loop snare 4: A snare 4 is used to 'thread the cannula' with the suture thread TH loaded on the spool 1 and is illustrated in FIGS. 2A, 2B, 2C, 6A, 6B and 7C. It comprises of a length of a pliable steel wire (or a filament of non metallic plastic material) 4WL. The wire 4WL is acutely folded, in a tight hairpin bend, in the middle or closer to one end forming a narrow distal tip 4T of double wire and 3-4 mm proximal to the tip 4T the two limbs of the wire loop are bent ipsilateraly to diverge away from each other thus resemble the letter 'Y'(when the wire is bent midway) or a 'hook' (when the wire is bent nearer one end to form a short limb 4SL and a long limb 4LL as illustrated in the FIGS. 6A and 6B) and the two proximal ends of the Y" shaped snare and the proximal end of the longer limb 4LL of the 'hook' shaped snare may be left unattached or may be removably or irremovably fixed to a metallic or plastic cylindrical grip 4G. The 'hook' shaped snare 4 or the 'Y' shaped snare with the two ends of the wire removed from a removable grip 4G has the advantage of easily snaring the suture thread and coming out free from the eye EY of a loop of thread TH-L as illustrated in the FIGS. 6A and 6B. The distal narrow tip 4T thus formed permits the snare 4 to be introduced into either the distal side hole 2SH or the proximal end hole 2PE of the cannula 2, and after emerging out of the opposite end of the cannula 2 the 'V' shaped snare 4 forms a small loop 4WL as illustrated in FIGS. 2B and 7C whereas a hook shaped snare 4 forms a hook 4SL as illustrated in FIG. 6A. The ligature end E then can be threaded onto the snare loop 4WL or the suture thread TH hooked by the hook 4SL to snare and subsequently maneuver the suture thread TH. The overall length of the snare 4 from the tip 4T to the proximal end fixed in the grip 4G is kept longer than the overall length of the cannula 2, to be threaded, by at least a few centimeters. The finest wire snare 4 that can be easily maneuvered and also easily handle the particular suture thread should be used so that the internal diameter of the cannula 2 can be minimized.

Procedure of Using the 'Device for Dispensing, Looping and Tying Ligatures'

The manner in which the device is employed for surgical ligations and the various aspects of usage and modifications are described stepwise as following:

a) Preparation of the Device for Surgical Purpose.
 b) Dispensing, Looping and Tying of the Ligature during Surgery.
   Single loop and overhand knot.
   Double loop or two turns of the same ligature.
   Two loops simultaneously and other known bends and hitches.

c) Modifications and Variations in the Design of the Device.

d) Reusing the Device for subsequent Surgery.

Preparation of the 'Device for Dispensing, Looping and Tying Ligatures' for Surgical Purpose:

For surgical use the device can be packed, labeled and sterilized before hand and shipped in several configurations viz. the ready to use device with the ligature pre-wound on the spool and threaded in the cannula; the device without any spool or with an empty spool; the spools individually with the required ligature pre wrapped; the different size cannulae individually along with the snare; the wire loop snare individually.

At the start of the operation the device is procured in the sterile field by the nurse. A device with the pre wrapped suture on the spool that is threaded through the cannula is ready for use but other configurations as mentioned above will require some preparation. An empty spool 1 on the device is wound with predetermined length of the required suture from a sterile reel uniformly and under sufficient tension and a spool 1 that is free is loaded with the ligature and mounted in the housing. The threading of the cannula is done subsequently as following.

Threading the Cannula with the Suture Thread:

The snare 4 is used to 'thread the cannula' with the suture thread TH loaded on the spool 1 and is illustrated in FIGS. 2A, 2B, 2C, 6A, 6B and 7C. The distal narrow tip 4T of the snare 4 is introduced into the distal side hole 2SH and threaded up the cannula 2 till the tip 4T and a small loop of wire 4WL emerges out from the proximal hole 2PH, close to the spool 1 as illustrated in FIG. 2B. The free end E of the suture thread TH wrapped on the spool 1 is then passed in the direction of the arrowheads, threading the wire loop 4WL, as shown in FIG. 2B. The spool 1 is allowed to rotate by keeping the finger RIF distant from the side guards 1SG of the spool 1, as shown in FIG. 3A. Now the wire loop snare 4 is completely withdrawn out of the cannula side hole 2SH. The free end E of the suture thread TH gets ensnared in the tip 4T of the snare 4 and is pulled out of the side hole 2SH threading the cannula as shown in FIG. 2C. The snare 4 is then removed to free the suture end E. By rotating the spool 1 in the appropriate direction by the side guards 1SG that project beyond the top edges TE, the extra length of suture thread TH emerging out of the side hole 2SH is wound back on the spool 1 leaving only a few centimeters of the suture thread TH presenting out of the side hole 2SH.

When the intention is to thread the cannula 2 with the suture thread TH wrapped on the spool 1 so that a loop of the suture thread TH-L presents out of the side hole 2SH then the snare 4 with one limb 4SL shorter and resembling a 'hook' is used as illustrated in FIGS. 6A and 6B. (A snare 4 with both limbs equal and long but unattached to a grip or a removable grip 4G can be also used). The distal narrow tip 4T of the snare 4 is introduced into the distal side hole 2SH and threaded up the cannula 2F, till the tip 4T and the short limb of wire 4SL emerge out from the proximal end 2PE, close to the spool 1 as illustrated in FIG. 6A. The ligature end E is held in the left hand LH and the suture thread TH is 'hooked' by the short limb 4SL of the snare 4. The snare 4 is completely withdrawn out of the cannula 2F and the distal side hole 2SH while the end E of the suture thread is withheld from entering the proximal end 2PE of the cannula 2F and the spool 1 is allowed to rotate freely and unwind. This maneuver will bring out a loop of suture thread TH-L from the distal side-hole 2SH with the free end E of the suture thread TH being held in the left hand LH thus remaining out of the proximal end 2PE of the cannula 2F as illustrated in FIG. 6B. The wire loop snare 4 is now removed from the eye EY of the loop TH-L of the suture thread TH as illustrated in FIG. 6B.

When the intention is to retrieve the end E of the suture thread TH passing once again a second time around the vein V as during the procedure of double looping a ligature that has already been looped once around the vein V (or to form other bends or hitches), then a funnel shaped' cannula 22 and a 'Y shaped' snare 4 is used, as illustrated in FIG. 7C. The snare 4 is introduced into the proximal open end 2PE of the cannula 22 and pushed in till it emerges out of the distal side hole 2SH and forms a small loop 4WL thereupon. The end of the ligature E is threaded into the snare loop 4WL and the snare is completely withdrawn out of the proximal end 2PE of the cannula 22 which snares the thread end E and threads it into the cannula 22. The cannula 22 is subsequently withdrawn from behind the vein to the left side that delivers out the threaded ligature that has been looped a second time around the vein V thereby completing the double loop around the vein V.

Dispensing, Looping and Tying Ligatures During Surgery:

The invention 'device for dispensing, looping and tying ligatures' is used in the following manner employing the 'novel technique' to dispense ligature, looping an exemplary tubular structure viz. a superficial vein V and finally tying a knot and ligate the vein V.

The manner in which to dispense—a single U loop and tie it in a overhand knot; double loop or pass two turns of the same ligature around the vein V; pass two loops alongside simultaneously around the vein V and also the possible use of the invention device to dispense several known bends and hitches is highlighted.

Dispense a Single 'U' Loop and Tie it in a Overhand Knot Ligating a Vein V:

i) The device, with the required suture thread TH wound on the spool 1 and then threaded through the cannula 2 with the end E and a short length of the suture thread TH visible and emerging out of the distal side hole 2SH near the tip of the cannula 2T, is held say in the right hand RH, without touching the spool 1 which is therefore free to rotate, as illustrated in FIG. 3A. The tip 2T of the cannula 2 is passed behind and across from say the right side to the left side of the vein V to the extent that the suture thread TH emerging out of the distal side-hole 2SH of the cannula 2 becomes visible on the left side of the vein V and the device is held stationary in this position without applying any traction on the vein V or the adjoining structures, as illustrated in FIG. 3A.

ii) The free end E of the ligature is grasped in the left hand LH as shown in FIG. 3A.

iii) The free end E is pulled up and away from the vein V, by the left hand LH to position marked X, to unwind the suture thread TH from the spool 1 and eventually withdraw and dispense the required length of the ligature loop LL on the left side of the vein V, as illustrated in FIG. 3A. As the suture thread TH when being pulled out of the cannula side hole 2SH traverses within the lumen 2L of the cannula 2 without coming in direct contact with the wall of the vein V or any adjoining structure, there is no graze, drag or sawing action of the ligature on the vein V or any adjoining structure.

iv) The free end E is held stationary in the left hand LH at position X without pulling the suture thread TH anymore, as in FIG. 3B. The invention device, with the thread 'unlocked' i.e. the spool permitted to rotate freely and unwind by keeping the right index finger RIF away from the side guards 1SG, is moved first to withdraw the distal tip 2T of the cannula to the right side of the vein V and subsequently away from the vein V in the direction of the arrows, as show in FIG. 3B. This movement tugs at the suture thread TH wrapped on the spool 1 making the spool to rotate and unwind to deliver and dispense the right limb RL out of the side hole 2SH of the cannula 2 and completes the U loop L around the vein V. Once an adequate length of the right limb RL of the ligature loop L that will suffice to tie knots is obtained, the device is not moved any further.

v) During the maneuver of dispensing the right limb RL of the ligature loop L the suture thread comes in intimate contact with the vein V but is static, hence there is no abrasive action of the suture thread TH on the vein V; but still some traction gets inadvertently applied to the vein V which depends upon the force required to pull the suture thread TH out of the side hole 2SH of the cannula 2 and rotate the spool 1 to unwind. To prevent even this minimal traction that gets inadvertently applied to the vein V while dispensing the right limb RL of the ligature loop L, the suture thread is held at the point marked Y in FIG. 3B, with a forceps, and at the same time the left limb LL of the loop L is slackened. This way very delicate and friable body structures can also be safely looped using the device.

vi) Eventually, a U loop L with sufficiently long limbs LL and RL on the two sides of the vein V is obtained, as shown in the FIGS. 3B and 4A.

vii) To tie the two limbs LL and RL together in a knot K, first the further release of the thread TH and its unwinding from the spool 1 is stopped, i.e. the thread TH is 'locked' by pressing with the index finger RIF on the uncovered projecting segments of the side guards 1SG of the spool 1, as shown by the two arrows in FIG. 4A. This permits the required tension to build up in the ligature loop L when the two limbs (RL and LL) are gently pulled with the necessary force so that the two limbs LL and RL can be tied together with sufficient tautness in a surgical knot K. Eventually, the knot K is tied ligating the vein V.

viii) The two limbs LL and RL of the ligature loop L above the knot K are cut with a scissors. The original left limb LL (with the former free end E) is inevitably discarded as waste because of its short length. But, the right limb RL, is still in continuity with the suture thread TH on the spool 1, is rewound by rotating the spool 1 by the side guards 1SG that project beyond the top edge TE, leaving only a few centimeters of the ligature end E coming out of the side hole 2SH. Thus the right limb RL that amounts to nearly half of the ligature loop L is saved and the device is ready for the next ligation.

Dispense a Double Loop i.e. Pass Two Turns of the Same Ligature Around a Vein V:

This may be done by two techniques; by using only a single invention device or by using two invention devices and a snare in cooperation.

Figure 7B:
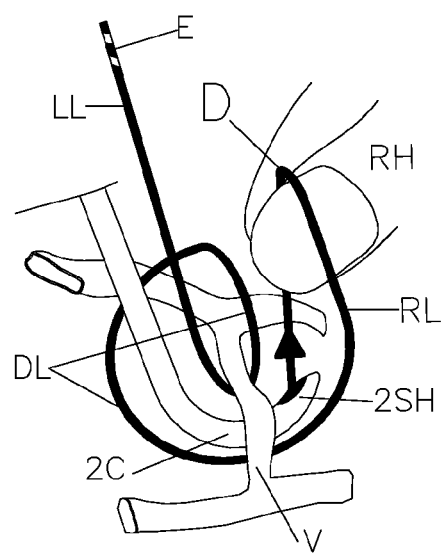
FIG. 7B is a perspective view to illustrate a single ligature being dispensed passing twice around the vein V in a double loop DL
Figure 7C:
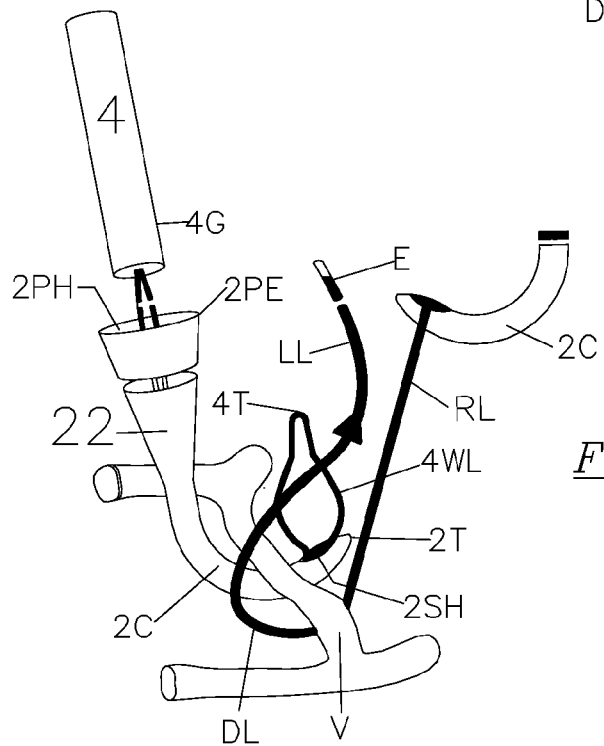
FIG. 7C is a perspective view to illustrate a ligature being dispensed around the vein V in a double loop DL utilizing an additional funnel shaped cannula 22 and snare 4.

Dispense a Double Loop Using One Invention Device Only:

i) The first step is to take a single 'U' loop around the vein by using the invention device as described in detail in the previous section and as illustrated in FIGS. 3A and 3B (with the difference that the right limb RL is kept shorter).

ii) The device is now on the right side and above the vein V with the right limb RL emerging out of the side hole 2SH and the tip 2T pointing to the left, as illustrated in FIG. 3B, is moved over to the left side and front of the vein V and rotated 180° in the vertical longitudinal axis so that now the tip 2T points to the right side of the vein V.

iii) The invention device is maneuvered so that the tip 2T of the cannula 2 is passed behind and across from the left side to the right side of the vein V (alongside the first U loop but in the opposite direction) to the extent that the suture thread TH emerging out of the distal side-hole 2SH of the cannula 2 becomes visible on the right side of the vein V and the device is held stationary in this position without applying any traction on the vein V or the adjoining structures, as illustrated in FIG. 7B.

iv) The suture thread TH emerging out of the distal side-hole 2SH of the cannula 2 is grasped in the right hand RH as shown in FIG. 7B.

v) The suture thread TH emerging out of the distal side-hole 2SH of the cannula 2 is pulled up and away from the vein V, by the right hand in a manner that the thread is dispensed from the spool 1 via the cannula 2 and the distal side-hole 2SH and without excessively pulling the ligature loop marked DL from the left side of the vein V to the right side of the vein V. After a sufficiently long right limb RL of the double ligature loop DL is dispensed on the right side of the vein V the suture thread TH is divided at the point marked D to finally complete the double loop DL looping around the vein V twice, with a left limb LL and a right limb RL, as illustrated in FIG. 7B.

vi) The invention device is removed by first withdrawing the distal tip 2T of the cannula to the left side of the vein V and subsequently away from the vein V. As the ligature emerging out of the side hole 2SH is already severed from the right limb RL it is immaterial whether the thread is 'locked' or 'unlocked' during this maneuver.

vii) The double loop may be used to ensnare the vein V to temporarily stop the flow of blood or the two limbs of the double loop may be tied in a knot using routine surgical techniques. The two limbs of the double loop are cut proximate to the knot and both limbs are discarded.

Dispense a Ligature Passing Around the Structure in Two or More Turns by Using Two Invention Devices and a Snare in Cooperation:

i) The first step is to take a single U loop around the vein by using the invention device as described in detail in the previous section and as illustrated in FIGS. 3A and 3B (the left limb LL and the right limb RL are kept as long as will suffice to tie knots and the latter is continuous with the suture thread TH on the spool 1).

ii) A second invention device is employed which can be of the exemplary embodiments as illustrated in FIGS. 1A, 1C and FIGS. 6A and 6B but preferably the device with the 'funnel' shaped cannula (preferably with the spool and the axle spindle removed) or only the funnel shaped cannula 2F, as illustrated in FIG. 7C, is used.

iii) The tip 2T of the cannula 22 (second device) is passed behind and across from the left side to the right side of the vein V (alongside the first U loop but in the opposite direction employed to dispense the first U' loop) to the extent that the distal side-hole 2SH of the cannula 22 becomes visible on the right side of the vein V and the device is held stationary in this position without applying any traction on the vein V or the adjoining structures, as illustrated in FIG. 7C.

iv) A snare 4 is then passed into the proximal end 2PE of the cannula 22 and pushed in sufficiently so that the tip 4T of the snare emerges out of the distal side hole 2SH and a small loop of wire 4WL is formed thereon as illustrated in FIG. 7C.

v) The end E of the left limb LL of the ligature is threaded into the small loop 4WL, as illustrated in FIG. 7C, and the snare 4 is completely withdrawn out of the proximal end 2PE of the cannula 22 which snares the thread and threads it into the cannula 22.

vi) The cannula 22 is completely withdrawn from behind the vein V to the left side and then away from the vein to deliver the threaded left limb LL of the ligature loop thus completing the double loop DL around the vein with the right limb RL emerging out of the side hole 2SH of the cannula 2 of the first invention device and the left limb LL is free and is the original end E of the suture thread TH.

vii) The double loop may be used to ensnare the vein V to temporarily stop the flow of blood or the two limbs of the double loop may be tied in a knot after 'locking' the thread i.e. stop the rotation of the spool 1, as illustrated in FIG. 4A. The two limbs of the double loop are cut proximate to the knot and only the left limb LL is discarded because the right limb RL is still in continuity with the suture thread TH on the spool 1 and is re-winded on to the spool 1 and thus saved.

viii) By serially repeating the aforementioned steps no. iii) to vi) the single ligature can be passed around the structure in any desired numbers of turns.

Two Methods to Pass Two Loops Simultaneously Alongside and Around the Vein V and the Possible Use of the Invention Device to Dispense Known Bends, and Hitches.

(i) First method: The cannula 2 of the device is threaded by the suture as usual but the length of suture thread TH emerging out of the side hole 2SH of the cannula 2 is kept long and the end E of the suture thread is held close to the spool 1.

(ii) The tip 2T of the cannula 2 is passed behind and across from the right side to the left side of the vein V to the extent that the suture thread TH coming out of the distal side-hole 2SH of the cannula 2 becomes visible on the left side of the vein V and the device is held stationary in this position and also the suture thread end E is held close to the spool on the right side of the vein V, as illustrated in FIG. 7A.

(iii) The suture thread TH emerging out of the distal side-hole 2SH of the cannula 2 is grasped in the left hand LH, as shown in FIG. 7A and is pulled up and away from the vein V, by the left hand in a manner that the thread is dispensed from the spool 1, via the cannula 2 and the distal side-hole 2SH, without pulling the ligature loop marked RL:1 (right limb of the first loop), on the right side of the vein V, to the left side of the vein V. After a sufficiently long left limb LL:1 of the first ligature loop LL-1 and a sufficiently long left limb LL:2 of the second ligature loop LL-2 are dispensed on the left side of the vein V, the ligature held in the left hand LH is not pulled anymore.

(iv) While holding the still continuous suture thread loop LL:1 and LL:2, with the left hand LH, on the left side of the vein V the invention device, with the thread 'unlocked' is moved first to withdraw the distal tip 2T of the cannula to the right side of the vein V and subsequently away from the vein V to deliver and dispense the right limb RL:2 out of the side hole 2SH of the cannula 2 and completes the second loop LL-2 around the vein V. Once an adequate length of the right limb RL:2 of the ligature loop LL-2 that will suffice to tie knots is obtained, the device is not moved any further.

(v) The suture thread is divided at the point marked D to finally separate and complete the two loops viz. the first ligature loop LL-1 comprising of left limb LL:1 on the left side of the vein V and the right limb RL:1 (with the original terminal end E of the suture thread TH) on the right side of the vein V and similarly the second ligature loop LL-2 comprising of the left limb LL:2 on the left side of the vein V and the right limb RL:2 on the right side of the vein V, as illustrated in FIG. 7A.

(vi) The two loops LL-1 and LL-2 may then be tied into knots by tying their respective left and the right limbs together and cutting the ligated loops proximate to the knots. Both limbs of the severed first ligature loop LL-1 are discarded and so is the left limb LL:2 of the second ligature loop LL-2. But the right limb RL:2 of the second loop L-2 is still continuous with the suture thread TH on the spool 1 and is re-wound on to the spool 1, to leave only a short length of the suture thread emerging out of the side hole 2SH of the cannula 2, thus saving suture material. Time is also saved as the two loops are dispensed at the same time and not serially and the two loops can be tied together simultaneously by two operators saving some more time.

(i) Second method: The first step is to bring out a loop of suture thread TH-L emerging out of the side hole 2SH of the cannula 2F using a 'hook' snare 4 as elaborated earlier in the section VII, (ii), a) 'Threading the cannula with the suture thread' and illustrated in the FIGS. 6A and 6B. The snare 4 is removed from the eye EY of the thread loop TH-L.

(ii) The tip 2T of the cannula 2F is passed behind and across from the right side to the left side of the vein V to the extent that the loop of suture thread TH-L emerging out of the distal side-hole 2SH of the cannula 2F becomes visible on the left side of the vein V and the device is held stationary in this position. The suture thread end E is held close to the spool 1, as illustrated in FIGS. 6B and 6C.

(iii) The suture thread loop TH-L emerging out of the side hole 2SH is pulled to gain suture thread from the spool 1 via the cannula 2F and the side hole 2SH and thus enlarge the 'eye' EY of the loop TH-L, while still holding the suture thread end E out of the proximal end 2PE of the cannula 2F as illustrated in FIG. 6B. (This loop TH-L will eventually form the two left limbs of the two ligature loops L-1 and L-2 when divided subsequently at the point marked '7' in FIGS. 6C and 6D).

(iv) While holding the still continuous suture thread loop TH-L on the left side of the vein V but releasing the end E of the suture thread TH, the invention device, with the thread 'unlocked', is moved first to withdraw the distal tip 2T of the cannula 2F to the right side of the vein V and subsequently away from the vein V. This delivers and dispenses the right limb (of the second loop L-2) out of the side hole 2SH of the cannula 2F and completes the second loop L-2 around the vein V and at the same time the end E of the suture thread is also delivered out of the side hole 2SH to become the right limb of the first loop L-1. Once an adequate length of the right limb of the ligature loop L-2 that will suffice to tie knots is obtained, the device is not moved any further.

(v) The loop TH-L is divided at point marked 7 to separate the two left limbs of the two ligature loops L-1 and L-2.

(vi) The two loops L-1 and L-2 may then be tied into knots by tying their respective left and the right limbs together and cutting the ligated loops proximate to the knots. Both limbs of the severed first ligature loop L-1 are discarded and so is the left limb of the second ligature loop L-2. But the right limb of the second loop L-2 is still continuous with the suture thread TH on the spool 1 and is re-wound on to the spool 1, to leave only a short length of the suture thread emerging out of the side hole 2SH of the cannula 2, thus saving suture material. Time is also saved as the two loops are dispensed at the same time and not serially which can be tied together simultaneously by two operators.

(vii) To form a 'cow hitch' around the vein V: The first four steps are performed in the same way as aforementioned and enumerate from (i) to (iv) except that the thread loop TH-L is not enlarged very much (step (iii)); the invention device is withdrawn from behind the vein V, to the extent that the tip of the cannula 2T crosses to the right side of the vein V, and is not moved very far from the vein (in contrast to step (iv)) but is brought in front of the vein V and the tip 2T and the side hole 2SH are passed into the 'eye' EY of the thread loop TH-L, as illustrated in FIG. 6D.

(viii) The suture end E of the suture thread TH that was held out of the proximal end 2PE of the cannula 2F close to the spool is released and the thread on the spool 1 of the invention device 'unlocked' i.e. the spool 1 permitted to rotate freely and unwind. The two threads (right limbs RL:1 and RL:2)

emerging out of the side hole 2SH are held and gradually pulled, at the point marked 9, to withdraw out the right limb RL:1 of the first loop L-1 that terminates in the suture end E out of the side hole 2SH; at the same time also dispense the right limb RL:2 of the second loop L-2 that unravels from the spool 1. The thread is cut at the point marked 8 to break the continuity of the right limb RL:2 of the second loop L-2 with the suture thread wrapped on the spool 1.

(ix) The two right limbs RL:1 and RL:2 pass through the eye of the loop TH-L as illustrated in FIG. 6D, are pulled to form the 'cow hitch' around the vein V.

(x) Using the invention device in the above mentioned technique (to dispense an exemplary 'cow hitch' around a vein V as illustrated in FIG. 6D), in conjunction with the previously mentioned technique (to dispense a double loop around a vein V as illustrated in FIG. 7C), using a second device and a snare in cooperation, and combining both above-mentioned techniques judiciously, it is conceivable to perform various known loops, bends, knots and hitches for surgical as well as for non-surgical uses.

Modifications in the Design of the 'Device for Dispensing, Looping and Tying Ligatures'.

The particular embodiments described and shown in the accompanying drawings are only illustrative and it is possible to conceive innumerable variations, applications, modifications, and extensions of the basic principles involved herein without departing from the scope and ambit of this invention. Many of the possible modifications have been described along with the aforementioned detailed description of the exemplary embodiments.

Reusing the 'Device for Dispensing, Looping and Tying Ligatures'

Predetermined length of suture that will just suffice for the particular operation is loaded on the spool. At the end of the procedure, the leftover ligature still wound on the spool is uncontaminated and untouched as it is protected within the confines of the housing. If the suture is re-sterilizable the thread is cut close to the spool and the spool with the left over thread is removed from the housing and re-sterilized and reused thereby saving suture. Similarly the device can be made of a material that permits repeated sterilization and used subsequently repeatedly.

The invention 'device for dispensing, looping and tying ligatures' can be used whenever ligatures are required and have to be looped around an object or passed through the object:

During all types of surgery including endoscopic surgery and robotic surgery.
In dentistry and daily use for dispensing dental floss or dental tape.
For tying identification and price tags.
In arts and crafts industry.
For sowing together materials like jute cloth or leather.
In electronic industry to dispense pliable wires during circuit designing.

ADVANTAGES OF THE INVENTION

The present invention device with the preloaded suture can be immediately used without any preparation especially during an emergency.

1. The cannula of the invention device has less diameter compared to the surgical clamps in use. Therefore less space and less dissection are required to negotiate the cannula around the structures and the blunt tip of the cannula itself can be used to create the required space which minimizes the chances of injury and saves time.

2. When using the present invention device, the ligatures are not grasped by any clamps therefore there is no risk of accidentally grasping a structure and injuring it.

3. When using the device the suture traverses in the cannula without grazing or dragging the structures, therefore wetting of the ligature is not important and there is less chance of injury.

4. As the suture is contained within the device itself, the chances of the suture to get entangled anywhere causing a jerk when it is being pulled in a loop and thus avulsing a delicate blood vessel are negligible when using the device.

5. Once the knot is tied and both limbs of the suture loop are cut proximate to the knot, only the distal free-limb of the ligature loop is discarded and the proximal limb which remains in continuity with the suture on the spool is wound back on the spool to be used again, thus saving almost half of the thread. Thus the consumption of the thread when using the device is nearly half compared to the conventional technique. Even the left over ligature on the spool at the end of the surgery can be reused after re-sterilization as it is not soiled being protected within the confines of the housing.

6. The angulation of the distal segment of the 'swivelable cannula' can be manually adjusted as per the contour of the structure being ligated, when negotiating the cannula tip behind and across the structure, which simplifies the procedure and minimizing the chances of injury.

7. The 'swivelable cannula' can be easily passed across endoscopic ports and even large diameter structures can be ligated during endoscopic surgery.

8. The honed cannula speedily dispenses ligatures passing through the structures.

Thus the invention 'device for dispensing, looping and tying ligatures' makes ligation—simpler, easier, faster, less traumatic, prevents complications, easy to perform during endoscopic and robotic surgery and economical consuming less suture material, in comparison to the conventional surgical technique of ligation.

The following discussion with reference to the FIGS. 8A to 17F elaborates the following:

1. Disadvantages and the limitations of the prior art curved clamps used universally for blunt dissection of tissues and structures and the comparative advantages of my invention when used for blunt dissection in both open and endoscopic procedures.

2. Disadvantages and the limitations of the prior art curved clamps and the ligature carriers used to deploy the ligature around the structure and the comparative advantages of my invention for said use in open and endoscopic procedures.

3. Disadvantages and the limitations of the prior art ligating devices and the comparative advantages of my invention in open and endoscopic procedures as a ligating device.

4. Disadvantages and the limitations of the prior art suturing devices viz. the 'suture-needle-needleholder' combination and the advantages of my invention in open and endoscopic procedures for suturing and the novel technique of 'continuous through and through suturing' that can be performed even through the lumen of a tubular or hollow structure.

5. The numerous applications and the wide scope of my invention in all open, endoscopic and robotic surgery and several non-surgical uses.

The following discussion and the accompanying illustrations during an open surgical procedure on drawing sheets 8/16, and endoscopic ligation on drawing sheets 10/16, 11/16 and 12/16 emphasizes the importance of the prerequisite blunt dissection or free preparation of the structure before the looping and the subsequent ligation of the structure can be pursued or even thought of. To attain the penultimate stage with the i) tissue dissected free and ii) the ligature properly positioned around the structure is the crux of every operation. The ultimate outcome of the surgical operation depends upon the safe and fast attainment of this penultimate stage and my invention helps to achieve it without depending on the conventional instruments. All prior art ligating devices ignore these 'could be fatal' and vital preliminary steps and as these prior art ligating devices are themselves incapable of performing the vital preliminary steps, they are dependent on the conventional instruments or the curved clamps. The several dangerous complications that are associated with these conventionally used curved clamps and how my invention provides a long awaited solution to this problem is highlighted in detail. Since the prior art ligating devices are only capable of fastening the specially prefabricated ligature and nothing else, they play only a minor role in the final outcome of the operation.

Furthermore the prior art ligating devices use very expensive specially prefabricated ligature and waste a lot of the suture material. The ligating devices are by themselves very expensive, intricate and their use involves unorthodox and complicated steps. The ligature may be already preformed into a closed 'O' shaped reducible loop by the deployed bulky slip knot or ball member or knotting element or similar devices. The pre-fabricated loop severely limits the utility of these ligating devices as only structures that have a free end can be ligated, which rules out all blood vessels and most of the other body structures too. Moreover the preformed loop can exclusively be only used for ligation and not for any other purpose for which ligature loops are commonly employed during surgery such as a tourniquet or for retracting or binding structures or passing the loop through the structure and not just around the structure. As these preformed loops with the slip knots or knotting elements; or bundle-strap type occlusion ties with their large retaining heads are of thick gauge and bulky hence, these ligating devices cannot be used for the ligation of fine structures for instance the very small and numerous side branches of the Saphenous Vein, a commonly used conduit for revascularisation during Coronary Artery Bypass Grafting (CABG) or for superficial structures as the ligatures and their fastening mechanisms will be palpable through the skin and be very irritating. Bundle-strap type occlusion ties can only be made from synthetic absorbable or non-absorbable material which have different handling characteristics compared to the commonly employed orthodox silk sutures for this purpose.

My invention uses the cheaper, conventional and customary ligatures which are familiar to every surgeon, without any wastage, without any prefabrication, for the ligation of all structures even if they do not possess a free end, whatever the size may be (including very fine less than a fraction of a millimetre size blood vessels) and dispenses ligature not only looping around the structure but also the more secure transfixion ligatures passing through the tissue in open, endoscopic or even robotic surgery. Moreover, the dispensed open 'U' shaped ligatures can be used for multiple purposes and not just for ligation. My device is also used for passing ligatures through the structures as a suturing device without the drawbacks of the conventional needle-needleholder combination. The technique of using my invention device is very easy to learn and practice in contrast to the very complex and unorthodox technique involved in the operation of the prior art devices, which ensures quick acceptance and the wide use of my invention. My invention device is simple and very cheap to manufacture and as customary ligatures are used it is very cost effective and versatile. My invention can dispense any pliable surgical/non surgical ligature/chord including pliable wires and ropes hence, has a very wide scope and utility and several non-surgical uses also.

Drawing Sheets 8/16 and 9/16:

The following example of Coronary Artery Bypass Grafting (CABG) epitomizes a very commonly performed surgical procedure and is discussed here to elucidate the wide scope and utility of my invention and the multiple uses of my invention in this procedure as following.

1. To free the Superior Venae Cava SVC from the adjoining Pulmonary Artery PA by performing blunt dissection, and then deploy an umbilical tape U in the created free space to form a 'U' loop around the Superior Venae Cava SVC that is used as a tourniquet.

2. To also loop the aorta AO with an umbilical tape AU for the purpose of retraction when clamping it (also loop the Inferior venae cava for snaring it which is not shown).

3. To securely, speedily and safely ligate, and then divide scores of side branches of the Saphenous Vein which is removed or harvested from the lower limbs and used as a conduit and grafted on the heart for CABG.

4. To pass stay or anchoring sutures PS through the Pericardium P used for the retraction of the Pericardium.

5. To dispense and fasten free ligatures L functioning as a free tie dispenser.

Looping the Superior Venae Cava SVC with an Umbilical Tape U Using My Invention device.

The two prerequisites for deploying the umbilical tape U (or any ligature) around the Superior Venae Cava SVC (or any structure) are:

i. A free space or room is required at the chosen site for the umbilical tape to dwell, which means that the Superior Venae Cava SVC has to be freed from the underlying Pulmonary Artery PA because the two are invariably stuck to each other by connective tissue.

ii. The umbilical tape U is eventually required to be positioned in the free space thus created, to form a 'U' loop with one limb of the open 'U' loop on either side of the Superior Venae Cava SVC.

FIG. 9A. depicts the conventional technique of looping the Superior Venae Cava SVC done by using a prior art curved clamp CC. Even though, the free space can be created by retracting the Superior Venae Cava SVC and cutting the connective tissue with scissors (sharp dissection) but this is too risky and may lead to either cutting the Superior Venae Cava SVC or the underlying Pulmonary Artery PA. Sharp dissection is however, done if the structures are bonded together with thick and strong, usually pathological connective tissue. Hence, blunt dissection is generally preferred in which the intervening connective tissues is gently teased out to separate the structures and thus create the free space. The conventional technique is to perform blunt dissection by using a curved clamp CC. The curved clamp CC is pushed behind the Superior Venae Cava SVC and moved back and forth and the jaws are alternately opened and closed which teases out the connective tissue and creates the free space. When the two jaws are opened the structures separate in the weakly adherent natural plane of cleavage in between the structures. But if the two jaws are opened too vigorously or the structures are very strongly adherent then instead of the connective tissue separating the wall of the structures can be torn. Once the free space is created, the curved clamp CC is placed in the free space and the two jaws are opened apart and then closed to grab the end of the umbilical tape U that is positioned within the said open jaws OJ by using a forceps F as depicted in FIG. 9A. The curved clamp CC is withdrawn to pull the end and half the length of the umbilical tape U behind and finally to the same side from which the curved clamp CC was passed to eventually form a 'U' loop passing around the Superior Venae Cava SVC.

This conventional technique employing the curved clamps suffers from many drawbacks that have been mentioned earlier. Two of these deadly complications are further exemplified in FIG. 9B and FIG. 9C and are also mentioned as pitfalls in most textbooks of operative cardiac surgery. (Please See 'CARDIAC SURGERY Safeguards and Pitfalls during Operative Technique', $2^{ND}$ Edition, by Siavosh Khonsari, Chapter 2, FIGS. 2-3, 2-4 and 2-7, Lippincott, Raven.)

Injury to the Superior Venae Cava SVC (FIG. 9B) and injury to the Pulmonary Artery PA (FIG. 9C) can happen when the curved clamp is negotiated in-between them and the jaws are opened; or after grasping the end of the umbilical tape U when the curved clamp CC is withdrawn which may injure the inadvertently grasped posterior wall W of the Superior Venae Cava SVC or the front wall WPA of the Pulmonary Artery PA resulting in massive blood loss and even death of the patient.

Because of these pitfalls, earlier attempts have been made to improve the curved clamps CC by devising 'ligature carriers' which are basically curved clamps but the two jaws touch each other on closure only at their tips. Proximal to the tip a gap is made in-between the two jaws, with the hope that only the ligature will be caught at the tip and the structures will be spared because of the gap. In clinical practice these ligature carriers are not used for dissection and can only be used to transfer the ligature from one side to the other and have the same drawbacks as their predecessors.

My invention with the 'swivelable cannula' and the blunt tip 2T as illustrated in FIG. 9D and drawing sheets 10/16, 11/16 and 12/16 provides an easy solution to safely and conveniently loop the Superior Venae Cava SVC without injuring the Superior Venae Cava SVC or the neighbouring Pulmonary Artery PA. The device is threaded with the umbilical tape U with a short length protruding out of the side hole 2SH. The tip of the cannula 2T is passed in between the Superior Venae Cava SVC and the Pulmonary Artery PA from below upwards as illustrated in the FIG. 9D so that eventually the tip 2T and the umbilical tape U emerging from the side hole 2SH are visible above the Superior Venae Cava SVC. Next, the umbilical tape U emerging from the side hole 2SH visible above the Superior Venae Cava SVC is simply held with the forceps F and the required length of the umbilical tape is pulled out, to dispense the upper limb of the ligature loop. Then the curved segment 2C and the tip 2T are gradually withdrawn from behind the Superior Venae Cava SVC and the device is moved up to dispense the lower limb of the 'U' loop and the required length of the tape is cut. The manner in which the possible movements of the cannula 2 are employed to loop the Superior Venae Cava SVC are similar to as elaborated in reference to drawing sheets 10/16, 11/16 and 12/16.

The two ends of the umbilical tape U may then passed through a plastic pipe SN (using a typical hook snare) and the umbilical tape U is held within the said snare at the desired position maintaining the desired tension in the loop by applying a clamp CL as shown in FIG. 9E. It is note worthy that the ligature loop dispensed by the prior art ligating devices cannot be used like a tourniquet in the above manner.

Similar technique, as used to loop the Superior Venae Cava SVC, is also employed to loop the Aorta AO as shown in FIG. 9D by the umbilical tape AL (and also the Inferior Venae Cava which is not illustrated) by using my invention device.

This looping of the Superior Venae Cava SVC or any other structure can be done easily and safely by my invention facilitated by the following salient features:

1. The closed and blunt rounded tip 2T.
2. The thinner curved segment 2C makes the passage easy and requires less room compared to the curved clamp CC and the additional space that is required by the curved clamps CC as the two jaws have to be opened to grasp the ligature, is also not necessary.
3. By using the swivelable cannula with the incorporated hinge joint mechanism HJ and utilising the many possible movements of the cannula 2, the tip 2T, can be easily made to 'wriggle through' in between the Superior Venae Cava SVC and the Pulmonary Artery PA by gently separating the connective tissue. In fact the curved segment 2C of my invention can be manipulated in such a way that it rotates in the axis of the superior venae cava revolving and just gliding on the surface of the Superior Venae Cava SVC. This is similar to a ring rotating around a finger, without any inward or outward force thus preventing injury.

It is obvious from the description that when looping a structure using my invention the complications, that occur when using the curved clamp CC as illustrated in FIG. 9B and FIG. 9C, cannot occur as my invention does not have any jaws to grasp and damage any structure.

The prior art ligating devices as they all lack the 'hinge mechanism and its actuating mechanism', the 'closed blunt tip and a side hole for the ligature to emerge out of the lumen' that are the salient features of my invention are absolutely incapable of any blunt dissection and thus are completely dependent on the conventional instrument to perform their tasks.

The Wide Scope and Application of My Invention as a Dissector to Dissect and Loop a Structure for Subsequent Ligation is Further Exemplified in the Surgical Ligation of a Patent Ductus Arteriosus (PDA).

PDA is one of the commonest congenital heart diseases, the first successful ligation of the PDA was performed in 1938, and since then millions of ligations have been done worldwide. Unfortunately even today cardiac surgeons are forced to practise the same age old and hazardous technique of employing a curved clamp or a right angle clamp in order to make a space all around the PDA and then grasp the end of the thick silk ligature and pull it to form a loop around the PDA and eventually ligate it. The wall of the PDA can be fragile and stuck to the adjoining aorta and the pulmonary artery. The pressure inside it is high and same as the blood pressure of the patient and attempts to loop it with the conventional curved clamps, many a times, ruptures the PDA with the resultant bleeding so vigorous that the entire chest cavity is inundated with blood within seconds and all the structures are obscured within the blood pool. Many lives have been lost because of rupture of the PDA during attempted looping with the curved clamps. (Please See 'CARDIAC SURGERY Safeguards and Pitfalls during Operative Technique', $2^{ND}$ Edition, by Siavosh Khonsari, Chapter 12, FIG. 12-5, Lippincott, Raven.)

Attempts to solve this problem have been futile and have only led to the abandonment of the closure of the PDA by 'ligation' by many surgeons who instead 'divide and stitch' the PDA which is actually a tedious and lengthy procedure with another set of new complications. In selected patients like the preterm neonate or infants in whom the PDA is very small, supple and not tense as these patients have much lower blood pressure, the PDA can be closed using surgical clips. Device closure as done by interventional cardiologist is the other solution but few patients are candidates for the procedure which has several possible complications some requiring emergency open surgery and the cost of the device is prohibitive in poorer and developing nations.

My invention device as explained above for looping the Superior Vena Cava SVC is the perfect solution to this difficult problem of looping the PDA for subsequent ligation. Moreover the device is capable of looping and ligating the PDA in both open ligation after a thoracotomy and also during endoscopic ligation of the PDA (explained later in 'the technique of endoscopic ligation' in reference to drawing sheets 10/16, 11/16 and 12/16). Prior art ligating devices either cannot be used for this procedure at all (ligating devices with the preformed loop) or are dependent on the prior art curved clamps for the dissection and looping of the PDA.

The Harvesting of the Saphenous Vein from the Lower Limb for CABG.

FIGS. 3A, 3B, 4A and 7B:

The Saphenous Vein runs from the ankle to the groin and has numerous side branches which have to be ligated and divided so that the Saphenous Vein may be removed or harvested. Some of the side branches can be as small as half a millimetre or even less in diameter and these branches are swathed in connective tissue. Due to the delicate nature and small size of the branches the dissection and the subsequent ligation has to be done very gently and carefully which requires utmost precision and concentration. Conventionally the fine branches are dissected and then looped by using small curved haemostats and subsequently ligated. This conventional technique has the same disadvantaged as mentioned earlier and many of these branches are avulsed and the resultant puncture hole must be repaired by expensive swaged sutures of polypropylene. These branches are ligated by using fine silk ligatures of size 3-zero or 4-zero (USP) that are 0.2 mm and 0.15 mm in diameter respectively. Silk is used because it is very supple and the knots are easily and securely tied. Every side branch has to be tied at two places (close to the Saphenous Vein and the farther end in the tissue) and then divided in-between the ligatures. These fine ligatures may open up in the postoperative period because of the arterial pulsations and the blood flow in the Saphenous Vein grafts causing bleeding around the heart that will require urgent re-exploration (a repeat surgery) for the securement of the bleeding branch. To prevent this deadly complication the side branches are ligated by two ligatures close to the main vein and that too by using a secure knot (not an easily undone slip knot as used by prior art ligating devices. The number of branches to be ligated depends upon many factors and may vary from a few to more than a score and as every branch has to be tied by three ligatures hence the number of ligations performed may vary from 10 to nearly 100 in a single operation to harvest the Saphenous Vein! Moreover, the poor hemodynamics i.e. the falling blood pressure (due to impending or ongoing heart attack) of the patient may not allow much time for the procedure and there may be a dearth of surgeons and assistants as the available operators are divided to either work on the heart in the chest or work in the leg to harvest the Saphenous Vein that will be required almost immediately.

None of the cited prior art ligating devices can be used for this purpose for the simple reason that the deployed prefabricated ligatures by these devices are not only very expensive (the cost of the ligature multiplied by the scores of ligation to be performed will amount to a very large sum) but also very thick (about half a millimetre or even more which can be thicker than the vein branch itself) and the 'fastened knots' (in the form of a slip knot or the ball member, the couple of knotting elements per ligature or the retaining heads of the bundle strap ties are very bulky and cumbersome and out of proportion to the delicate side branches of the Saphenous Vein.

My invention device with a fine 'J' shaped cannula, a closed blunt tip 2T and a side hole 2SH for the ligature to emerge out of the threaded cannula and the spool loaded with an adequate length of 3-zero or 4-zero silk suture is the ideal and long awaited solution for this procedure. My invention can speedily dissect and loop the small vein branches then help to ligate them with very secure knots employing the time tested orthodox ligature and technique saving time, effort, money and also lives. The procedure of ligating a small vein is illustrated in FIGS. 3A, 3B, 4A and 7B has been already explained. Besides, the technique of simultaneously deploying two ligature loops around the vein branch that can be simultaneously tied by two operators as depicted in FIG. 7A further shortens the time required for harvesting the Saphenous Vein.

Passing Pericardial Stay Sutures PS and Tying Free Ligatures L Using My Invention Device.

Drawing Sheet 9/16:

The five diagrams illustrated on this drawing sheet and the following discussion exemplifies two other uses of my invention in addition to the already mentioned uses in the previous discussion. The technique of passing pericardial stay sutures PS using my invention device and the advantages thereof over the conventional technique employing conventional instruments (needle-needleholders) and tying free ligatures L using my invention is elucidated.

To deploy ligatures passing through the Pericardium P to be used as pericardial stay sutures PS for retracting the pericardium and expose the heart, my invention device with the distal curved segment 2C, and a sharp needle tip 2ST, with or without an incorporated hinge mechanism is used. The appropriate ligature is threaded into the cannula and a short length emerges out of the distal side hole 2SH.

Figure 10A:
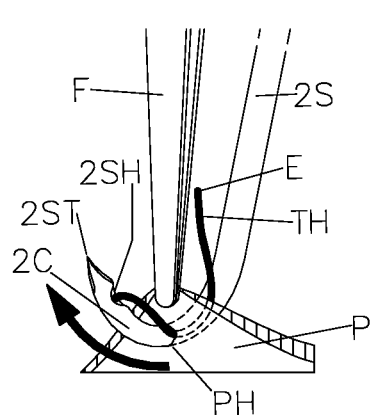
FIG. 10A depicts the cannula tip 2ST passed through the Pericardium P being held by a forceps F.

FIG. 10A: depicts the edge of the Pericardium P held and lifted up with a tissue forceps F. The sharp tip 2ST and the distal portion of the curved segment 2C is passed through the Pericardium P in the direction of the curved arrow till the thread TH emerging out of the side hole 2SH is visible on the left side in front of the Pericardium P.

Figure 10B:
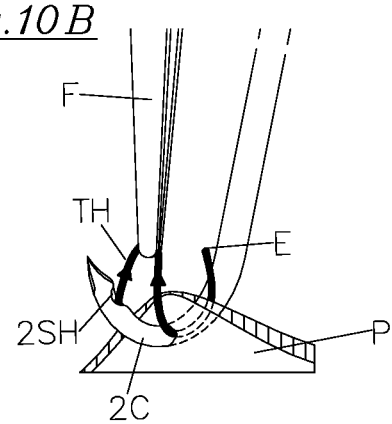
FIG. 10B depicts the ligature TH being withdrawn out by the forceps F.

FIG. 10B: The tissue forceps releases the pericardial edge and 'picks up' the thread TH emerging out of the side hole 2SH. The Pericardium P once released remains suspended on the curved segment 2C of the cannula without falling back on the heart.

Figure 10C:
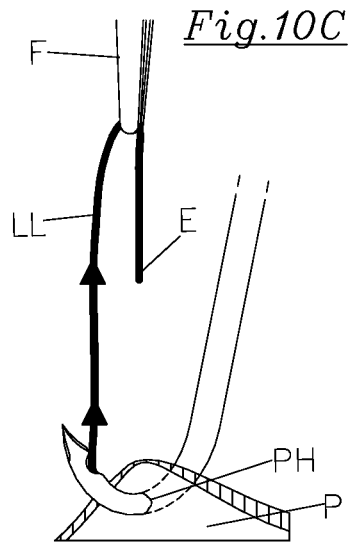
FIG. 10C depicts the dispensing of the left limb LL of the pericardial stay suture.

FIG. 10C: the ligature is withdrawn and pulled up by the tissue forceps F till the required length of the left limb LL is obtained.

Figure 10D:
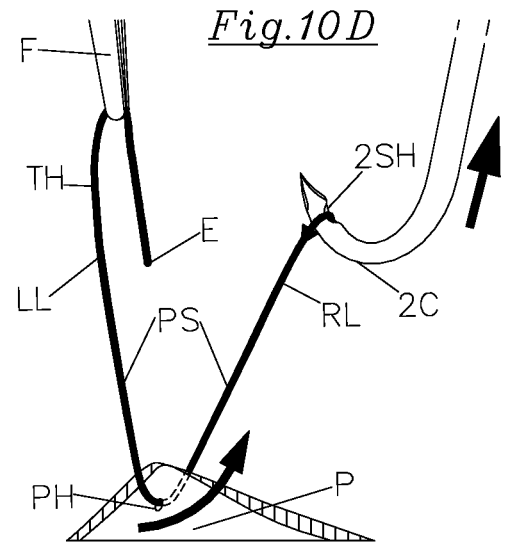
FIG. 10D depicts the dispensing of right limb RL of the pericardial stay suture.

FIG. 10D: to dispense the right limb of the ligature the cannula is completely withdrawn out of the Pericardium P and moved up, while the thread is permitted to be dispensed, and the left limb LL is held stationary with the tissue forceps.

The two limbs LL and RL may then be tied together anchoring the Pericardium P to the sternal retractor. The right limb RL may also be passed again through the skin edges and anchored to the skin.

The ligature is cut, and without any further preparation the device is ready to deploy the next pericardial stay suture as generally six to eight such sutures are employed in every surgery.

Conventionally pericardial stay sutures are deployed using the prior art trio combination of 'suture-needle-needleholder' as following:

The needle (eyeless with the swaged suture or with the suture threaded through the eye) is held in the needle holder either in the fore-hand or in the back-hand grip. The pericardium is held with the tissue forceps and the needle is then partially driven through, say from the back to the front of the pericardium. The needle holder is removed from the needle, which is left dangling in the pericardium and the needle holder is again reapplied to hold the needle near its tip in front of the pericardium. The needle is pulled out completely thus passing the ligature through the pericardium and forming the loop.

The prior art surgical technique, just mentioned specifically for deploying pericardial stay sutures, employing the trio combination of 'suture-needle-needleholder' has several disadvantages all of which are successfully remedied by employing the novel technique using my invention as following:

1. Once the needle has been partially passed into the pericardium the needle is released by the needleholder so that it may be reapplied on the needle near its tip. This often pulls out the needle from the pericardium thus causing unnecessary repetition of the steps which is very frustrating to the surgeon.

2. After the needle has been released, before the needle holder can be reapplied to hold the needle, the pericardial edge held with the forceps gets accidentally released or slips because of the faulty tissue forceps and falls back on to the heart and may also:

i. Remove the needle from the pericardium and misplace it.
 ii. The needle may penetrate the top wall of the heart causing bleeding or arrhythmias.
 iii. The pericardial edge has to be picked up with the tissue forceps.

3. The needle may be difficult to grab when the needle holder is reapplied because the needle may move when dangling in the pericardium due to the transmitted cardiac pulsations. The direction of the needle may also change due to magnetization when the needle holder is brought close.

4. Because of the above difficulty many surgeons do not release the needle from the needle holder but instead release the pericardial edge which now gets suspended on the needle held in the needle holder and then hold the needle with the tissue forceps in front of the pericardium before releasing the needle from the needle holder and then pull out the needle with the tissue forceps. The tissue forceps are designed to hold tissues and not hard needles. Holding the needle with a tissue forceps repeatedly ruins the tissue forceps which are expensive instrument.

5. The needleholder may grasp the needle too close to the tip which will ruin the needle permanently and thus compel a new needle and suture to be taken.

Besides the abovementioned drawbacks pertinent to the specific task of passing pericardial stay sutures, there are numerous universal disadvantages of the conventional technique of using the prior art trio combination of 'suture-needle-needleholder' which are all remedied advantageously by using my invention device as following:

1) Problems concerning the suture:
 a) The nuisance due to the long length of the suture trailing the conventional needle is avoided.
   i) The suture thread is contained in the spool 1 and thus not liable to entangle in the objects in the surgical field.
   ii) Assistant to follow the thread trailing the needle is not required.
   iii) The entire length of the suture following the needle is not required to be passed and transferred from one side of the tissue to the other side.
   iv) Tangles formed due to the 'memory effect' of the packaging on the suture are avoided.
 b) A very long length of ligature contained on the spool 1 is available that can be repeatedly dispensed. In contrast, conventionally only limited lengths of the threaded or swaged sutures is available which may be consumed in just a single stay suture and thus require a new ligature every time. The frustration and time spent in procuring new ligature every time is avoided when using my invention.
 c) The 'short stumps' that are discarded in the conventional technique are not formed when using my invention hence wastage of expensive suture is avoided.

2) Problems concerning the needle:
 a) Swaged or an eye needle is not required when using my invention which leads to the following advantages:
   i) Saves the cost of the needle.
   ii) Saves the time required to thread every suture bit through the needle.
   iii) Needle prick may be accidentally caused when handling the needle that can transmit many deadly diseases like AIDS or Hepatitis B.
   iv) Threading braided suture through the eye of the needle is time consuming and it becomes very frustrating if the braids at the end of the suture unravel and especially if the nurse is naive, nervous or has intention tremors. All this is avoided when using my device. The cannula 2 is threaded once and the wrapped suture on the spool is sufficient for the entire surgery.
   v) Time wasted by the premature removal of the thread and re-threading the needle is avoided with my device.
 b) The teeth in the jaws of the needle holders damage the needle and the rough needle when passed through the tissues in turn damages the tissues, this does not happen, when my invention device is used.
 c) A meticulous needle count has to be maintained throughout the operation which is avoided.
 d) There is no possibility of the needle being misplaced, lost, or left behind within the body cavity of the patient when using my invention. The time wasted and the frustration in searching for a missing needle and the x-rays and other investigations done to locate the needle are thus avoided.

3) Problems concerning the needleholder: The needle holder is not required when using my invention which leads to the following advantages:
 a) Saves the cost of the needle holder which must be replaced periodically due to the wear and tear of the jaws and the ratchet lock.
 b) Fixing and holding the needle in the needle holder is avoided. This is a precise act and an art that requires focus and concentration and is difficult if the nurse is naive, nervous or has intention tremors.
 c) Time spent in fixing the needle to the needle holder is saved.
 d) The direction in which the needle tip points when the needle is fixed in the needle holder and can be either for a back-hand stitch or a fore-hand stitch is very crucial which is dictated by the location of the structure being sutured and the personal preference of individual surgeons (that adds to the confusion).

It is very frustrating for the surgeon when he gets the needle pointing in the wrong direction and distracts him from the main step of the operation. This is a big advantage of my device which can be conveniently used in taking both forehand and backhand suture by the surgeon and saves the nurse from a major botheration.

(e) The ratchet lock present in the needle holders may malfunction making the needle jump at times or may be too hard to lock or unlock.

f) The needle may wobble in the needle holder due to wear and tear of the jaws leading to the following complications when suturing, are avoided with my invention device:
  i) Extra time is spent in taking the suture bites.
  ii) Injury and damage to the structure through which the suture bite is being taken or injury to a neighbouring structure.
  iii) Imprecise placement of the suture in the structure and creation of a large hole leading to complications.
  iv) Frustration to the surgeon.

These above-mentioned problems with the trio combination of prior art suture-needle-needleholder have persisted since the dawn of surgery. Attempts of solving the problems have been futile and have only come so far in the form of swaged needles that only solve the problem of threading the needle. These swaged needles are expensive and for the routine tasks like passing stay sutures majority of institutes world over continue to use the eye needle because of the lower cost. Measures to make the needles less wobbly include improved needle design and improved grip of the needle holders (which are very expensive) but still the problem persists.

My Invention Provides a Suitable Alternative to the Conventional Prior Art Trio Combination of 'Suture-Needle-Needleholder'.

Figure 10E:
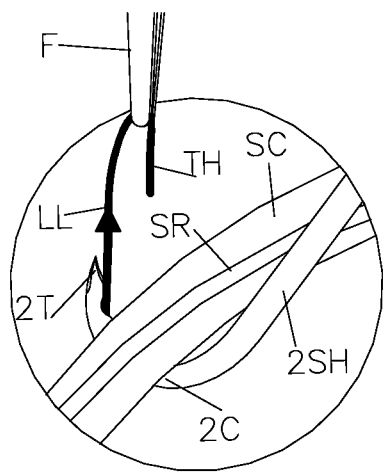
FIG. 10E depicts the ligature LL being tied around the snare SR and the Superior Venae Cava Cannula SC.

FIG. 10E depicts the ligature LL being tied around the snare SR and the superior venae cava cannula SC. Numerous free ligature ties also are required during CABG and these ties can be very conveniently dispensed looping around the structures or the objects even if located at a depth, to be tied subsequently.

The wide scope and utility of my invention, in contrast to the prior art ligating devices, and the advantages of my invention device compared to the conventional prior art curved clamps and the prior art trio combination of 'suture-needle-needleholder' are thus clearly demonstrated by the exemplified surgical procedures of CABG and PDA ligation in the preceding discussion and the illustrations on drawing sheets 8/16 and 9/16.

Endoscopic Ligation Using My Invention

In the abdominal cavity (and the entire body) all organs are enveloped and bound to its neighbour and/or the body wall by connective tissue. The very first step of any operation is to liberate the tissue or the organ from the connective tissue so that the actual procedure (which may be ligation, excision suturing etc.) on that tissue/organ can be performed. This process of dissection of the tissue or the organ is tedious and the difficult step of the operation and likely to cause injury to the tissues and organs which can lead to major complications and death of the patient.

The restricted manoeuvrability during endoscopic procedures makes this dissection very difficult and at times forcing the procedure to be converted to an open procedure thus depriving the patient the advantages of smaller incisions and faster recovery times of endoscopic surgery.

The figures on the drawing sheets, 10/16, 11/16 and 12/16 illustrate the novel technique of endoscopic ligation of a vein using my invention device with the 'swivelable cannula'. The technique of using my device firstly to perform blunt dissection and then secondly to loop the ligature around the vein so that the loop can be finally fastened to ligate the vein is illustrated in detail.

In this exemplified common scenario, it will be almost impossible for the conventional curved clamps to dissect the vein (unlike during open surgery in the previously mentioned examples of dissecting and looping the superior venae cava SVC and the Patent Ductus Arteriosus).

Figure 11A:
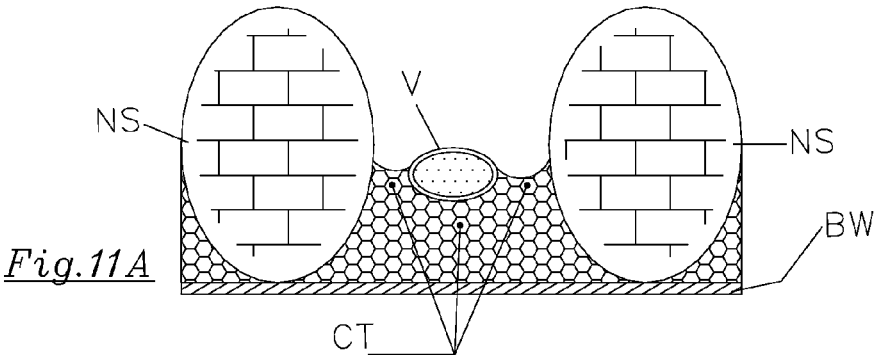
FIG. 11A diagrammatically depicts the abdominal cavity partially in cross section and the vein V to be ligated is stuck to the neighbouring structures NS and to the underlying back wall BW by connective tissue CT (honeycomb hatch). The front wall of the abdominal cavity is not shown.

Drawing Sheet 10/16:

FIG. 11A is a diagrammatic partial cross section of the abdominal cavity and illustrates a vein V juxtaposed in between two very close neighbouring structures NS which are relatively rigid and immovable (wall hatch, acting like two walls), and the vein V is attached to the neighbouring structure NS on either sides and also to the back wall BW (angular line hatch) by connective tissue CT (honeycomb hatch).

Figure 11B:
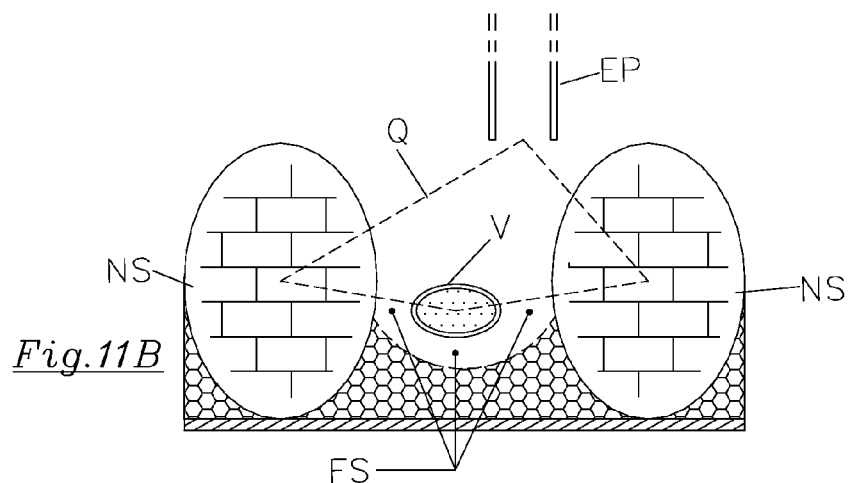
FIG. 11B depicts the vein V separated by free space FS (for the ligature to reside), from the neighbouring structures NS and the back wall BW, made by blunt dissection, which is the first step in ligation of the vein V. The endoscopic port EP is shown in cross section.

FIG. 11B illustrates an endoscopic port EP in cross section that has been positioned in the abdominal cavity. The diameter of the vein is larger than the internal diameter or the lumen of the endoscopic port EP. The dashed-line quadrilateral Q passing through the centres of the vein V and the neighbouring structures NS and the centre of the inner end of the endoscopic port EP defines the relative position of these structures to one another and is not altered in the subsequent figures so that it can be amply illustrated that even in this almost impossible situation by using and only manipulating my invention device (without even the need to move the endoscopic port EP which would provide even more manoeuvrability) the vein V can be looped easily and subsequently ligated.

The first essential step of ligation is to free the vein V from the neighbouring structure NS on both sides and the underlying back wall BW achieved by blunt dissection and thus create a circumferential free space FS all around the vein V as illustrated in FIG. 11B. Conventionally this is achieved by using endoscopic dissectors that have two jaws, and are used in a similar way as the curved clamps CC as explained in FIG. 9A. The endoscopic port EP limits the size of the endoscopic dissector that can be introduced and consequently the size of the diameter of the vein that can be looped endoscopically; unlike in the open procedure of looping where large size curved clamps CC may be used. The disadvantages, as already elucidate, of these dissectors is that opening and closing of the jaws and then moving the instrument back and forth may tear the inadvertently grasped vein V (particularly in the region behind the vein V that is poorly or not at all visualised through the endoscope). The neighbouring structures NS may also be grasped within the two jaws and injured.

Figure 11C:
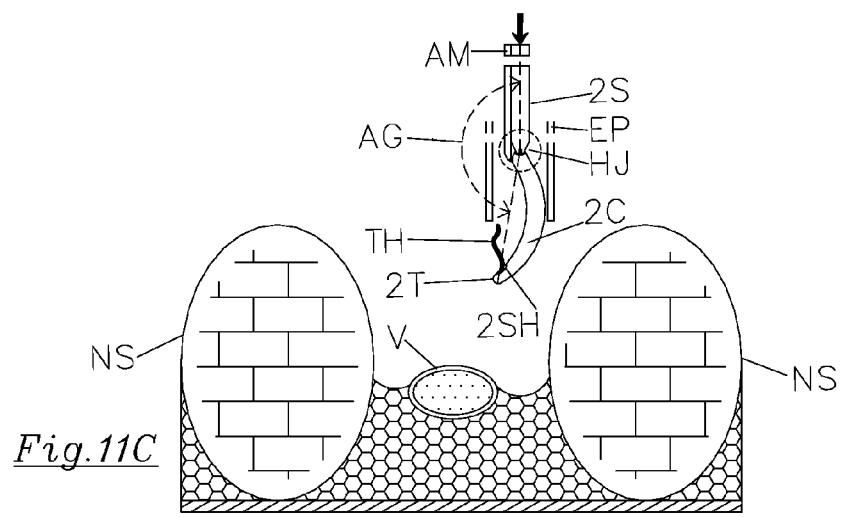
FIG. 11C depicts the invention device being negotiated across the endoscopic port EP.

FIG. 11C illustrates the invention device comprising the 'swivelable cannula' incorporating the hinge mechanism HJ with a blunt tip 2T and already threaded with the ligature TH being passed across the endoscopic port EP into the abdominal cavity. As mentioned earlier the diameter of the vein V is more than the internal diameter of the endoscopic port EP and the vein V to be successfully ligated will have to be looped by a invention device having a proportionally large sized distal curved segment 2C which will thus have a transverse extent greater than the internal diameter of the endoscopic port EP. This is the reason why the vein cannot be dissected and looped using the conventional curved clamp because the large curved segment will not be able to pass through the endoscopic port EP.

Without the presence of the hinge mechanism HJ the long curved segment 2C of my invention device will also be unable to pass across the endoscopic port EP. The hinge mechanism permits the distal curved segment 2C to be aligned with the proximal segment 2S of the cannula in a straight end to end configuration thereby reducing the lateral extent of the device and in this straightened configuration the large distal curved segment 2C can be easily passed across the endoscopic port EP as shown in the FIG. 11C. Conversely the distal curved segment may be completely folded on to the proximal segment to decrease its lateral dimension.

Incorporation of the hinge mechanism coupled to the incorporated actuating mechanism which can be operated to change the angle between the distal segment of the cannula 2C and the proximal segment 2S is a non-obvious solution to the above problem.

Drawing Sheet 11/16:

FIG. 12A illustrates the negotiation of the distal curved segment 2C and the distal blunt tip 2T in-between the vein V and the neighbouring structure NS on the right side in order to create the free space FS. This region between the vein V and the neighbouring structure NS on the right side as seen in the FIG. 12A is a vertical drop and to match the contour of the vein V the angle AG (dashed-line arc) of the distal curved segment 2C to the proximal segment 2S is made 'vertical in almost straight alignment' to the proximal segment 2S. The distal blunt tip 2T is gently pushed down with rotatory movement as illustrated by the curved arrows, which 'drills' the tip into the connective tissue CT and creates the free space FS freeing the vein V from its neighbour NS on the right side.

FIG. 12B illustrates the negotiation of the distal curved segment 2C and the distal tip 2T below the vein V separating it from the back wall BW and thus creating the free space FS below the vein V that is continuous with free space FS created earlier on the right side. As can be visualised the lower wall of the vein V is more or less horizontal. To match the contour of this lower wall of the vein V the angle AG (dashed-line arc) of the distal curved segment 2C to the proximal segment 2S is diminished from the initial position in FIG. 12A. Rotating the device as illustrated by the curved arrows at the top will sweep and create a horizontal plane of free space FS under the vein V.

Once the curved segment 2C and the tip 2T of the cannula 2 are positioned below the vein V as shown in FIG. 12B, just by decreasing the angle AG of the distal curved segment 2C to the proximal segment 2S and/or slight withdrawal of the device out of the endoscopic port EP will tend to lift the vein V as shown by the arrow on the vein V that will further help in separating the lower wall of the vein V from the underlying body wall BW.

As my invention device comprises of only one single tube (in contrast to the more than one concentric tubes that may be incorporated as in the prior art ligating devices) the proximal segment 2S can be made as thin as technology permits (the thickness depends upon the diameter of the carried suture TH to be dispensed and the technique used to thread the cannula for example using vacuum or any other known method like a snare). This spares additional room within the endoscopic port EP for the device to be moved in the horizontal plane, in the direction of the horizontal arrows as illustrated in FIG. 12B, towards or away from the vein V. This movement of the curved segment 2C when placed under the vein V further helps in the separation of the lower wall of the vein V from the underlying body wall BW. Furthermore, a small tilt i.e. rotation of the cannula in the horizontal axis within the endoscopic port EP is also possible because of the thin cannula 2 as shown by the angle VAG (dashed small arc).

All these possible movements of the proximal segment 2S, as illustrated in FIG. 12B, viz. the vertical up-down movement and the rotatory movement in the vertical axis; the lateral left-right movement and the forward-backward movements and the possible small tilt i.e. rotation in the horizontal axis within the endoscopic port EP are transmitted with full fidelity to the distal curved segment 2C and can be further modulated by decreasing or increasing the angle AG of the distal curved segment 2C to the proximal segment 2S at the incorporated 'hinge mechanism HJ' by operating the actuating mechanism AM. Hence all these aforementioned possible movements of my invention device as illustrated in FIG. 12B, and coupling with the inherently possible small amount of movement of the endoscopic port EP positioned within the body permit the dissection of the vein V easily even in this difficult situation.

FIG. 12C illustrates the negotiation of the distal curved segment 2C and the distal tip 2T further around the vein V so as to free the vein V from the neighbouring structure NS on the left side and thus creating the free space FS on the left side of the vein that is continuous with the free space FS below and the right side of the vein V. This is achieved by further diminishing the angle AG of the distal curved segment 2C to the proximal segment 2S so that the tip 2T points upwards and utilizing a combination of the various possible movements as elucidated in FIG. 12B.

Figure 14A:
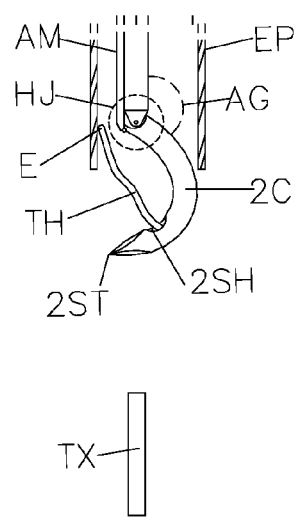
FIG. 14A diagrammatically depicts a tissue TX within the body cavity and the invention device being negotiated through the endoscopic port EP (shown in cross section). The body wall is not shown.
Figure 14B:
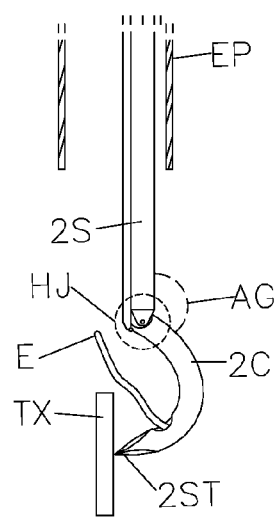
FIG. 14B depicts the invention device advanced into the body cavity and the sharp needle tip 2ST is positioned at the point of entry on the right side of the tissue TX.
Figure 14C:
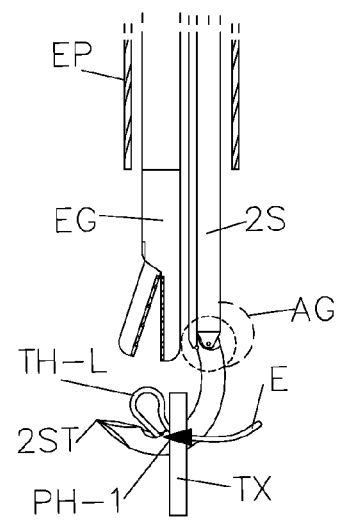
FIG. 14C depicts the angle AG (dashed arc) has been increased to drive the tip 2ST through the tissue TX and an endoscopic grasper EG advanced through the endoscopic port EP.

Once the tip 2T and the thread TH emerging out of the side hole 2SH are visible on the left side of the vein V the thread TH is grasped with a endoscopic grasper or forceps (that may be passed through a different endoscopic port or through the same endoscopic port EP (as illustrated in FIG. 14C on drawing sheet 13/16) to pull up the thread TH and dispense the left limb LL of the 'U' loop.

Another advantage of my device is noteworthy that the ligature TH when pulled up in order to dispense the left limb LL of the ligature loop, because it moves within the lumen of the cannula 2, neither causes any abrasion of the vein V nor apply upward traction on the vein V which may both lead to the injury of the vein V.

Drawing Sheet 12/16:

FIG. 13A: illustrates the withdrawal of the tip 2T and the curved segment 2C from the left side of the vein V, to a position below the vein V. To achieve this withdrawal, the angle AG of the distal curved segment 2C to the proximal segment 2S is now increased (to the same degree as in FIG. 12B), and the device moved to the right in the direction of the horizontal arrow and the device is pulled, a little, upwards and out of the endoscopic port EP in the direction of the top vertical arrow. As the left limb LL of the ligature is held in a fixed position more of the ligature thread TH is withdrawn out of the side hole 2SH of the cannula 2 on moving the device in the abovementioned manner.

FIG. 13B illustrates that as the straight segment 2S of the device is further withdrawn out in the direction of the top vertical arrow the angle AG of the distal curved segment 2C to the proximal segment 2S is further increased (to the same degree as illustrated in FIG. 12A) so that the tip 2T points downwards and this manoeuvre withdraws the tip 2T to the right side of the vein V.

FIG. 13C illustrates the curved segment 2C being withdrawn out of the endoscopic port EP resulting in the dispensing of the right limb RL of the ligature 'U' loop.

Now after the two limbs LL and RL have been dispensed on the respective left and right side of the vein V and if the left limb LL has also been brought out of the same endoscopic port EP (or transferred from a different endoscopic port), then the two limbs LL and RL of the ligature loop can be tied together using the conventional 'extra-corporeal' surgical technique utilizing a knot pusher.

The two limbs LL and RL may be also fastened together by other known means of prior art also. The two limbs LL and RL of the ligature loop can be also tied together using the conventional 'intra-corporeal' surgical technique.

Before the knot is tied the right limb of the ligature RL coming out of the side hole 2SH may also be once again passed around the vein V by a similar technique utilized and demonstrated in drawing sheet 14/16 to ligate the vein V by a figure-of-eight ligature or a double ligature for extra security.
Deploying Sutures Passing Through Structures Endoscopically and Endoscopic Suturing Using My Device.

The prior art ligating devices can only perform endoscopic ligation and are incapable of suturing of any sort! The following discussion again elucidates the advantages of using my invention during endoscopic surgery for passing a 'single suture' (drawing sheet 13/16), 'transfixion suture' (drawing sheet 14/16) and 'continuous through and through suturing' (drawing sheet 15/16 and 16/16).

It will be clear that my invention overcomes the drawbacks and provides an alternative to the prior art conventional 'suture-needle-needleholder' combination in endoscopic surgery also just like in open surgery (explained previously in reference to figures on drawing sheet 9/16). My invention can also be used during surgeries utilising 'mini incisions' ('key hole' surgeries). The device can be easily adapted to be used during robotic surgery.

In these endoscopic or 'key hole' surgical procedures, the main reason of the difficulty in passing sutures through a tissue is the severe restriction of magnitude or even negation of the various movements of the conventional needle holder that the surgeon employs to orient and move the needle relative to the tissue being sutured. Using my 'swivelable' invention device (with a distal curved segment 2C with the needle sharp tip 2ST and a side hole 2SH and an incorporated hinge mechanism HJ and the incorporated actuating mechanism AM) enables the surgeon to change the angle AG between the proximal segment 2S and the distal curved segment 2C of the cannula 2 to precisely align and move the tip 2ST of the curved segment 2C (now functioning as the needle) through the tissue TX.

One major advantage of using my invention over the trio combination of suture-needle-needle holder is that there is no risk of the needle getting lost within the body cavity.
Passing a Single Suture Through a Tissue Endoscopically.
Drawing Sheet 13/16:

Illustrates the novel technique of taking a single suture bite endoscopically passing through a tissue TX.

As mentioned earlier even long curved segments 2C can be easily passed across the endoscopic port EP in the 'straight narrow alignment'.

FIG. 14A diagrammatically depicts the tissue TX to be sutured within the body cavity and the endoscopic port EP shown in cross section has been placed in. The threaded, honed and 'swivelable' cannula is being introduced through the endoscopic port EP with the angle AG such that the proximal segment 2S and the distal curved segment 2C are in 'straight narrow alignment' (like in FIG. 11C).

FIG. 14B illustrates the tip 2ST positioned close to the tissue TX aimed at the point of entry and the distal part of the curved segment 2C in somewhat perpendicular orientation to the tissue TX.

Figure 14D:
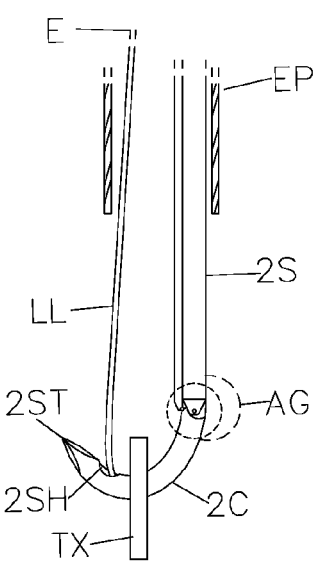
FIG. 14D depicts the dispensed left limb LL.

FIG. 14C illustrates the tip 2ST and the distal part of the curved segment 2C having penetrated across the tissue TX just by altering (increasing) the angle AG of the distal curved segment 2C to the proximal segment 2S as shown by the dashed arc. An endoscopic grasper EG has been passed through the same (or can be a different) endoscopic port EP to grasp the loop of thread TH-L emerging out of the side hole 2SH and pull up the loop of thread TH-L to dispense the left limb LL as illustrated in FIG. 14D.

Figure 14E:
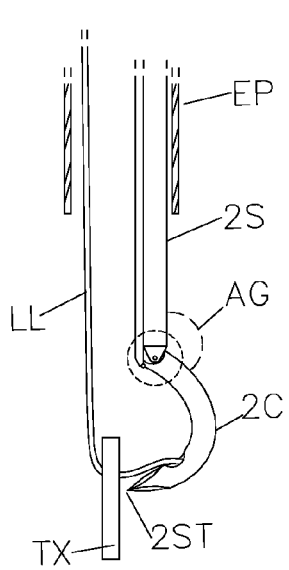
FIG. 14E depicts the decreased angle AG and the withdrawn tip 2ST on the right side of the tissue TX.

FIG. 14E illustrates the tip 2ST and the distal part of the curved segment 2C having been withdrawn out of the tissue TX by simply altering (decreasing) the angle AG of the distal curved segment 2C to the proximal straight segment 2S.

Figure 14F:
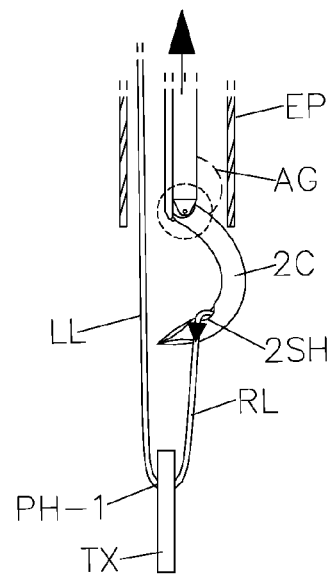
FIG. 14F depicts the dispensing of the right limb RL.

FIG. 14F illustrates the curved segment 2C having been pulled up into the endoscopic port EP after it is aligned to the proximal straight segment 2S in a 'straight narrow configuration' by altering the angle AG so that it can be subsequently withdrawn out of the endoscopic port EP, which also dispenses the right limb RL of the loop.

After the two limbs LL and RL have been dispensed they can be fastened together in the conventional surgical technique by tying knots or by using other means of fastening or further manipulated as required for example in passing a figure of eight suture as explained in context to figures on the drawing sheet 14/16.

Passing of a Figure of Eight ('Double Loop' or 'Transfixion' Ligature) Ligature Loop Around a structure endoscopically.
Drawing Sheet 14/16:

The figures illustrate the passing of a figure of eight ('double loop' or 'transfixion' ligature) ligature loop around a vein V that is embedded in and attached to a tissue TX through the endoscopic port EP by using the invention device with a 'swivelable cannula' having a needle sharp tip 2ST.

The advantages of the 'figure of eight' or a double loop 'transfixion' suture are:
1. the added security,
2. less chances of 'cutting through' of the vein V because of the cushioning effect of the included extra tissue within the ligature,
3. avoids the dissection of the vein V that may lead to injuring the vein and cause bleeding,
4. Prevents the migration of the ligature loop and its slippage out of the cut end of the vein V and the resultant bleeding.

Analogous situations arise during laparoscopic surgery when the vascular pedicel of an organ or tissue has to be first ligated and subsequently divided.

As has been mentioned earlier that it is difficult to pass even a single ligature through tissues endoscopically using the prior art trio combination of suture-needle-needle holder, passing a figure of eight ligature is even more difficult. It is a fairly simple task when using my invention as illustrated on the drawing sheet 14/16 and explained now.

Figure 15A:
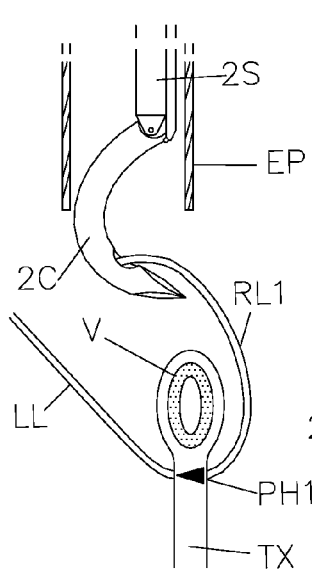
FIG. 15A diagrammatically depicts the already deployed first loop, with left limb LL and right limb RL1, passed through the puncture hole PH1 in the pedicel tissue TX, located within the body cavity, that incorporates the vein V (shown in cross section) to be ligated by a transfixion ligature, through the endoscopic port EP.

FIG. 15A illustrates the vein V (shown in cross section) embedded in the pedicel of tissue TX. The vein V has been already looped once (in the manner explained earlier and illustrated on drawing sheet 13/16). The puncture hole PH1 in the tissue TX below the vein, through which the bottom part of the loop is passing, was created by passing the tip 2ST and the distal part of the curved segment 2C in the direction of the arrowhead i.e. from right to left. Subsequently the cannula 2 has been rotated by 180° so that now the tip 2ST points to the right.

The endoscopic port EP as shown here in cross section is omitted from the subsequent diagrams for the sake of simplicity.

Figure 15B:
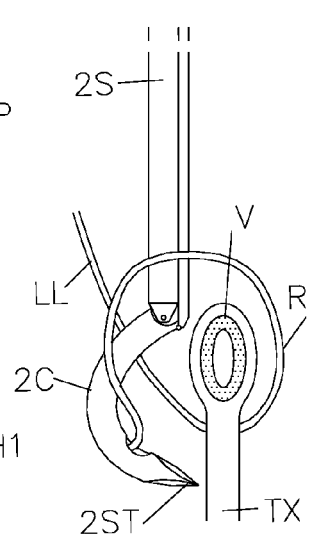
FIG. 15B depicts the tip 2ST placed near the point of second entry into the tissue TX on its left side.

FIG. 15B illustrates the cannula tip 2ST placed a little below the first puncture hole PH1 on the left side of the pedicel tissue TX in preparation of the second puncture hole and loop TH-L.

Figure 15C:
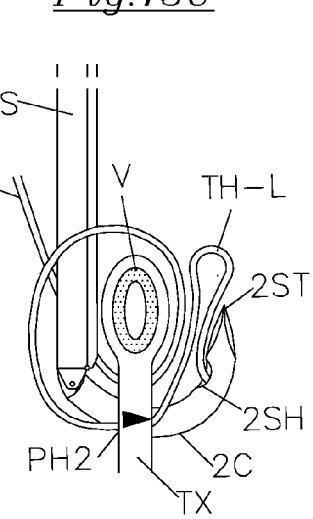
FIG. 15C depicts the tip 2ST pierced across the tissue TX through the second puncture hole PH2.

FIG. 15C illustrates the cannula tip 2ST and the distal part of the curved segment 2C passed through the tissue TX creating the second puncture hole PH2 below the first puncture hole PH1 and the loop of thread TH-L is visible on the right side of the tissue TX emerging out of the side hole 2SH. Passing the tip 2ST through and across the tissue is again achieved by simply altering the angle between the proximal segment 2S and the distal curved segment 2C as explained earlier.

Figure 15D:
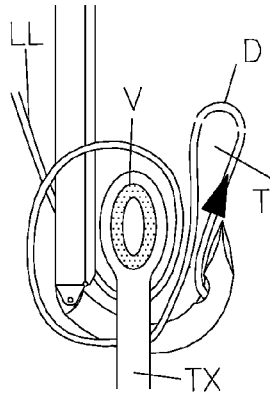
FIG. 15D depicts the ligature loop TH-L being enlarged and will be finally cut at point D.

FIG. 15D illustrates the thread loop TH-L being pulled up and enlarged (by using an endoscopic grasper or a conventional nerve hook, not shown in the diagram) by withdrawing out suture thread from the cannula 2 as shown by the arrow head. The loop TH-L is enlarged till a sufficient length of ligature is obtained (may be even enlarged and brought out of the same endoscopic port through which the cannula 2 has been passed or a different one) and severed at the top D.

Figure 15E:
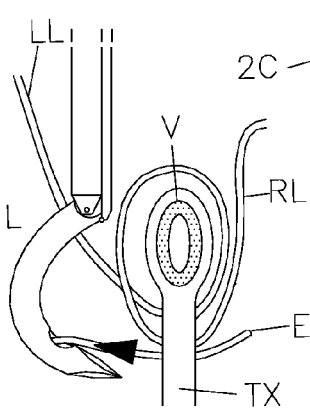
FIG. 15E depicts the tip 2ST withdrawn and the ligature end E being withdrawn out of the tissue TX.

FIG. 15E: The ligature end E is withdrawn from the tissue TX by rewinding it on to the spool 1 or it is simply pulled out of the proximal end of the cannula 2 leaving only the end E and the terminal few centimetres of the thread outside the side hole 2SH of the cannula. The tip 2ST and the distal part of the curved segment 2C are withdrawn out of the tissue TX by simply altering the angle of the distal curved segment 2C to the proximal straight segment 2S as explained earlier.

Figure 15F:
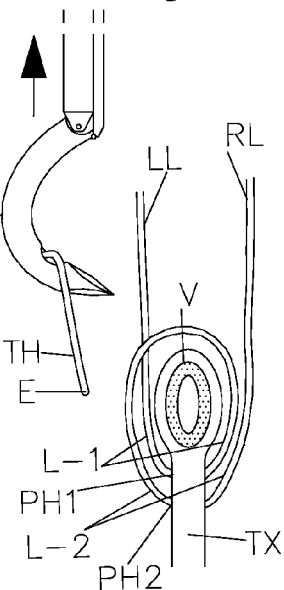
FIG. 15F depicts the device being withdrawn and the two loops L-1 and L-2 looped around the vein V.

FIG. 15F: The cannula is withdrawn out of the endoscopic port and the two limbs LL and RL of the ligature loop are fastened together thereby ligating the vein V by a 'double' or 'figure of eight' or 'transfixion ligature'.

The Novel Technique of 'Continuous Through and Through' Suturing.

Drawing Sheet 15/16:

The illustrations on drawing sheet 15/16 exemplify the novel technique of 'continuous through and through' suturing of two tissues T1 and T2 (starting from the top) using the 'swivelable' cannula with a needle sharp tip 2ST, endoscopically.

FIG. 16A illustrates the first loop comprising the left limb LL and the right limb RL has been already dispensed passing through the first puncture holes PH1 (created in the direction of the arrow head) in the adjacent tissues T1 and T2 to be sutured.

The endoscope port EP depicted in cross section is not illustrated in subsequent diagrams.

FIG. 16B illustrates the sharp tip 2ST and the distal part of the curved segment 2C has been again passed through the adjacent tissues T1 and T2 through the second puncture hole PH2 made at an appropriate distance below the first puncture hole PH1 and in the same direction i.e. from right to left as shown by the arrow head. Subsequently the thread loop TL2 is enlarged by pulling it up using an endoscopic grasper or a nerve hook.

FIG. 16C: In the next step the end E of the left limb LL of the thread is passed into the thread loop TL2 and the left limb LL is pulled through the thread loop TL2.

FIG. 16D: In the next step the tip 2ST and the distal part of the curved segment 2C is withdrawn out of the tissues T1 and T2 which is easily accomplished by altering the angle of the distal curved segment 2C with respect to the proximal segment 2S as explained earlier. Now the thread TH passing through the cannula 2 is rewound on to the spool 1 or pulled out through the proximal end of the cannula 2 so that the thread loop TL2 is reduced to an extent that it is just pulled into the second puncture hole PH2 and as a result the proximal part (the part close to the tissue T1) of the left limb LL also gets pulled into the second puncture hole PH2 (similar to FIG. 17F) while the end E of the suture and the remaining length of the left limb LL (beyond the suture segment LL1) remains outside on the left side of tissue T1. Counter tension is applied on the end E of the left limb LL to prevent the ligature (beyond the proximal segment LL1 of the left limb LL) getting pulled to the right side of tissue T2 beyond the puncture hole PH2. These steps lay the suture segment LL1 on the left side of tissue T1 and the suture segment RL1 on the right side of tissue T2 simultaneously.

FIG. 16E: The next step is similar and a repetition of the step explained above in FIG. 16B as the sharp tip 2ST and the distal part of the curved segment 2C is once again passed through the adjacent tissues T1 and T2 through the third puncture hole PH3 made at an appropriate distance below the second puncture hole PH2 and in the same direction as the second puncture hole PH2 i.e. from right to left as shown by the arrow head.

The next step is to enlarge the thread loop TL3 (in the same manner as illustrated in FIG. 16B) and then pass the end E of the thread into the thread loop TL3 (in the same manner as illustrated in FIG. 16C) and pull the left limb LL through the thread loop TL3. The thread loop TL3 is reduced now or after the cannula is withdrawn out of the puncture hole PH3 (similar to FIG. 16D). These steps lay the suture segment LL2 on the left side of tissue T1 and the suture segment RL2 on the right side of tissue T2 simultaneously (as shown in FIG. 17E on drawing sheet 16/16).

The above steps are repeated as necessary to suture together the required lengths of the tissues T1 and T2 ensuring the right tension in the suture line by applying matching and appropriate tension to the free end E of the left limb LL of the suture on the left side of the tissue T1 and the thread TH emerging out of the side hole 2SH (the original right limb RL of the loop) on the right side of the tissue T2.

Finally, after the two tissues T1 and T2 have been sutured in this continuous manner the remnants of the two limbs LL and RL of the ligature loop are fastened together by any known technique.

It can be appreciated that the novel technique and the invention can be used with comparative ease in a similar manner for 'continuous through and through' suturing in all open procedures also.

It can also be appreciated that the invention device always remains on the same i.e. the right side of the tissue T2 and the thread loops are manipulated on the left side of the tissue T1. Hence, this technique can be advantageously used when suturing hollow organs or tubular grafts with the invention device inserted into the lumen and working from within the lumen for e.g. in intestinal anastomosis or repair of aortic dissection. Additional tissue or synthetic material may be incorporated in the suture line on the outside of these hollow structures by sequentially passing it through the thread loops TL1, TL2, TL3 . . . to strengthen the suture line and make the anastomosis leak proof. The same suturing technique may also be applied for non-surgical uses also.

Drawing Sheet 16/16:

Drawing Sheet 16/16: illustrates the conventional technique of 'continuous through and through suturing' (starting from the top) using the prior art trio combination of 'suture-needle-needle holder' in an open non-endoscopic operation. The same may be attempted endoscopically but it is immensely difficulty and next to impossible.

The difference in the conventional technique and my novel technique are also highlighted.

FIG. 17A, FIG. 17B, FIG. 17C and FIG. 17D: The first suture S1 is laid by the following steps and the successive sutures S2, S3, S4 and so on are laid by the sequential repetition of the same steps:

1. The needle N held in the needle holder NH in the back-hand grip is passed from the left side of tissue T1 through the puncture hole PH1, so that the needle is visible on the right side of tissue T2.

2. The needle N is released by the needle holder NH and left hanging in the tissues and re-grasped by the needle holder NH in the same back-hand grip near the tip of the needle N on the right side of tissue T2.

3. The needle N is withdrawn out completely and the length of trailing suture TRL is pulled all the way to leave only the left limb LL on the left side of the tissue T1.

4. The needle N is repositioned in the needle holder NH in the fore-hand grip.

5. The needle N is passed into tissues, at an appropriate distance from puncture hole PH1 from the right side of tissue T2 making the puncture hole PH2, so that part of the needle is visible on the left side of tissue T1.

6. The needle N is released by the needle holder NH and left hanging in the tissues within PH2 and re grasped by the needle holder NH in the same fore-hand grip near the tip of the needle on the left side of tissue T1.

7. The needle N is withdrawn out and the length of trailing suture TRL is pulled all the way thus laying the first stitch S1 on the right side of tissue T2 and leaving the left limb LL on the left side of the tissue T1.

8. The needle N is repositioned in the needle holder NH in the back-hand grip and passed through the tissues through the puncture hole PH3 at an appropriate distance from puncture hole PH2 as illustrated by the arrow head from left to right and the above steps are repeated to lay the second stitch S2 on the left side of the tissue T1.

9. Similarly the third stitch S3 (which starts the return journey) is laid by passing the needle N and the trailing suture TRL through the puncture hole PH4 which is placed adjacent to puncture hole PH2 as shown in FIG. 17C and FIG. 17D. The needle N must not be passed through the puncture hole PH2 which can cause the needle to 'lance' through the suture already present there and thereby cut or weaken it and also prevent the sutures to be pulled to provide the required tension in the suture line.

10. Similarly the fourth stitch S4 is laid by passing the needle N and the trailing suture TRL through the puncture hole PH5 which is placed adjacent to puncture hole PH1 as shown in FIG. 17C taking the above mentioned precaution and this completes the suture line with the limb LL on the left side of tissue T1 and the trailing suture TRL on the right side of the tissue T2, as shown in FIG. 17C.

11. The above mentioned two limbs LL and the trailing suture TRL may be fastened together in a surgical knot or by employing any of the fastening devices of prior art.

FIG. 17E illustrates the completed continuous through and through suturing of the two tissues T1 and T2 sutured by the novel technique with my device (starting from bottom and finishing at the top) to compare it with the conventional technique of continuous through and through suturing using the trio of 'suture-needle-needle holder' as illustrated in FIG. 17C (starting from top, going to the bottom and then finishing at the top).

FIG. 17F is the magnified partly cross section view of the encircled region of FIG. 17E. The sutures are passing through the same puncture hole PH2 and are inter locked in contrast to the FIG. 17D which is a similar view of the encircled region of FIG. 17B in which the sutures are parallel in their separate puncture holes PH4 and PH2.

The advantages of my invention devise when used for suturing are obvious and have been highlighted in the earlier section of taking stay sutures as illustrated on sheet 9/16 and arise particularly due to the avoidance of the universal drawbacks of the conventional trio of 'suture-needle-needle holder' combination.

My novel technique of 'continuous through and through suturing' has the additional advantages over the conventional technique of 'continuous through and through suturing' using the conventional trio of 'suture-needle-needle holder' combination as following:

1. As the suturing is done and continues in one direction from one end to the other hence the frequent readjustment of the endoscope and structures is not required, whereas, when suturing using the conventional trio of 'suture-needle-needle holder' combination for 'continuous through and through suturing' the direction of suturing is from one end to the other end and then back to the same end requires frequent readjustments.

2. The transfer of needle N from one side of the tissues to other side of the tissues being sutured is particularly avoided, which as explained earlier is the most difficult step during endoscopic suturing.

3. A major disadvantage of the conventional continuous through and through suturing using the trio of 'suture-needle-needle holder' during endoscopic surgery or open surgery is that the entire length of the trailing suture TRL has to be pulled and transferred to the side of the needle N which is sequentially passed from one side of the tissues to the other side as shown in FIG. 17A and FIG. 17B.

Even in open surgery when suturing using the trio of 'suture-needle-needle holder' it is difficult to manage the long trailing thread TRL and requires an assistant who follows and manages the thread by keeping the loops of the trailing suture TRL away from the suturing site. It is understandably lot more difficult and almost impossible during endoscopic surgery considering the severe restriction of space and limitation of manoeuvrability.

When suturing using my invention the short segment of suture comprising only of the left limb LL has to be managed in the above mentioned manner as the remaining length of the suture is contained within the lumen of the cannula (as shown in FIG. 16B, FIG. 16C, FIG. 16D and FIG. 16E) and wrapped on the spool 1 disposed near the proximal end 2PE of the cannula 2. The right limb RL and the left limb LL of the ligature loops always continue to remain on their same respective sides of the tissue and do not crossover completely which makes the suturing using my device very easy.

1. In the conventional technique of suturing, each time the needle is passed fully across the tissues it only lays down the stitch on the side of the needle from which it is passed as shown in FIG. 17A, FIG. 17B and FIG. 17C.

2. It is clear that the conventional technique due to the above-mentioned drawback will require almost double the number of puncture holes; 5 puncture holes PH1 to PH5 as shown in FIG. 17C in contrast to 3 puncture holes PH1 to PH3 in FIG. 17E. In the conventional technique the puncture holes have to be placed precisely and accurately so that the tissues are covered by stitches on both sides avoiding any uncovered areas and the needle must not pass through the earlier puncture holes as this may damage and cut the earlier stitch.

3. It is very difficult to readjust the tension in the suture line as the suture segments are laid on the two sides of the tissue alternately and it cannot be discerned whether the suture segment was laid while going up or going down along the suture line.

In contrast to the conventional technique of 'continuous through and through suturing' using the suture-needle-needle holder combination, the novel technique of 'continuous through and through suturing' using my invention has the following advantages:

1) Requires only half the number of puncture holes in the same direction only and thus half the effort and double the speed.

2) Only the tip 2ST and a small length of the distal curved segment 2C are passed through the tissues unlike the entire needle N.

3) With each puncture hole the curved segment 2C is only partially passed across the tissues T1 and T2 in my novel technique and it results in both sides of the tissues being covered with suture segments as shown in FIG. 16E in which the puncture hole PH2 (and the steps described) lays down the segment LL1 on the left side of tissue T1 and the segment RL1 on the right side of tissue T2. The puncture holes in the tissues are all made from the same side and will always lay down simultaneously the segment LL1, LL2, LL3 ... on the left side of tissue T1 and the corresponding and equal segment RL1, RL2, RL3 ... on the right side of tissue (as shown in FIG. 16E and FIG. 17E), therefore there will be no uncovered portion of tissue in the suture line which makes the suture seam very strong.

4) It is very easy to readjust the tension in the suture line and in fact may be conveniently left for the end as the penultimate step to tying the limbs of the ligature. This is due to the fact that the suture segments are laid in one direction and the ligature limbs LL and RL remain on the same respective sides.

The terms and expressions used in this specification, to describe the invention in specific detail and exemplify the manner in which it may be carried into practice, are of description and are not limitative to the scope of this invention, as it is not intended by the use of such terms to exclude any equivalents of the features herein illustrated and described. Furthermore, the particular embodiment described and shown in the accompanying drawings is only illustrative and it is possible to conceive innumerable variations, applications, modifications, and extensions of the basic principles involved herein without departing from the scope and ambit of this invention.

I claim:

1. A device, comprising:
    a cannula having a proximal end, a distal end, and a lumen extending between the proximal end and the distal end, wherein the distal end is closed and is in a form of a sharp tip;
    a hinge provided between the proximal end and the distal end, the hinge including an actuating means for altering an angle of the hinge between a resultant distal segment and a resultant proximal segment of the cannula;
    a side hole, in the distal segment proximal to the distal end of the cannula such that the side hole communicates with the lumen;
    a spool for winding a suture thread thereon, the spool comprising a hub and side guards disposed on either side of the hub, and when the spool is rotating to dispense the suture thread, a first portion of a length of the suture thread extends within the lumen of the cannula such that the first portion of the length of the suture thread is covered and a second portion of the length of the suture thread protrudes from the side hole;
    a housing that rotatably and removably houses the spool and is removably coupled to the proximal end of the cannula allowing the cannula to be rotated about a longitudinal axis, wherein the housing is at least partially uncovered for permitting visualization of the spool; and
    a lock-unlock mechanism configured to regulate dispensing of the suture thread in a controlled manner, wherein the lock-unlock mechanism includes at least one side guard, from the side guards, of the spool projecting beyond an edge of the housing, the lock-unlock mechanism being usable to lock the spool by placing a finger on the at least one side guard to hamper partially or to stop completely a rotation of the spool, and the lock-unlock mechanism being usable to unlock the spool by removing the finger away from the side guards to allow the spool to passively rotate when a controlled amount of tension is applied to the suture thread emerging from the spool.

2. The device as claimed in claim 1, wherein the lock-unlock mechanism comprises a segment of the at least one side guard of the spool.

3. The device as claimed in claim 1, wherein the lock-unlock mechanism further comprises a mechanical or an electromechanical mechanism.

4. The device as claimed in claim 3, wherein the mechanical or the electromechanical mechanism acts either on the spool or the suture thread, or both the spool and the suture thread.

5. The device as claimed in claim 1, wherein the side guards and the hub forms an annular channel adapted to carry a length of suture thread.

6. The device as claimed in claim 1, further comprising two side-arms of the housing extending radially beyond and covering the at least one side guard.

7. The device as claimed in claim 1, wherein at least one hole is made in the hub, and at least one hole is made in the at least one side guard of the spool.

8. The device as claimed in claim 1, wherein the housing is made in a U-shape with two parallel facing side arms that converge and fuse to a central base, and wherein the proximal end of the cannula is removably coupled to the central base.

9. The device as claimed in claim 1, wherein the housing is made in a U-shape with two parallel facing side arms that converge and fuse to a central base, and wherein the spool is rotatably and removably disposed between the two parallel facing side arms.

10. A method of suturing employing the device as claimed in claim 1, the method comprising:
    positioning a needle tip of the cannula at a first point of an intended suture line on a first side of a structure to be sutured;
    altering the angle between the proximal segment and the distal segment of the cannula at the hinge of the cannula by manipulating the actuating means of the hinge to push the needle tip and the side hole through the structure to the opposite side of the structure creating a first puncture hole;
    dispensing the suture thread by allowing the spool to rotate and pulling a first loop of suture thread emerging out of the side hole of the cannula to transfer a distal end of the suture thread and a first length of the suture thread to a side opposite to the first side of the structure;
    restraining the distal end and the first length of the suture thread on the opposite side of the structure; and
    further dispensing the suture thread and re-altering the angle between the proximal and the distal segment of the cannula at the hinge of the cannula by manipulating the actuating means of the hinge to withdraw the needle tip and the distal segment of the cannula from the first puncture hole to the first side of the structure.

11. The method as claimed in claim 10, further comprising:
    positioning the needle tip of the cannula at a second point of the intended suture line on the first side of the structure;
    altering the angle between the proximal and the distal segment of the cannula at the hinge of the cannula by manipulating the actuating means of the hinge to push the needle tip and the side hole through the structure to the opposite side of the structure to create a second puncture hole;

restraining the distal end and the first length of the suture thread on the opposite side of the structure;

pulling the loop of suture thread emerging out of the side hole of the cannula to draw a length of suture thread and form a second loop of the suture thread on the opposite side of the structure, wherein the distal end of the suture thread and the first length of the suture thread are passed through the second loop of the suture thread;

restraining, on the opposite side of the structure, the distal end of the suture thread and the first length of the suture thread which is passing through the second loop of suture thread;

re-altering the angle between the proximal and the distal segment of the cannula at the hinge of the cannula by manipulating the actuating means of the hinge to withdraw the needle tip and the distal segment of the cannula from the second puncture hole to the first side of the structure; and reducing the second loop of the suture thread on the opposite side of the structure by rewinding the suture thread on the spool and generating tension in a first stitch that passes through the first puncture hole and second puncture hole, wherein the first stitch is formed by the interlocking of the first length of the suture thread and the second loop of the suture thread in the second puncture hole.

12. The method as claimed in claim 11, further comprising:
positioning the needle tip of the cannula at a third point of the intended suture line on the first side of the structure;

altering the angle between the proximal and the distal segment of the cannula at the hinge of the cannula by manipulating the actuating means of the hinge to push the needle tip and the side hole through the structure to the opposite side of the structure creating a third puncture hole;

restraining, on the opposite side of the structure, the distal end of the suture thread and the first length of the suture thread, which is interlocked within the first stitch at the second puncture hole;

pulling the loop of suture thread emerging out of the side hole of the cannula to draw a length of suture thread and form a third loop of the suture thread on the opposite side of the structure, wherein the distal end of the suture thread and the first length of the suture thread are passed through the third loop of the suture thread;

restraining, on the opposite side of the structure, the distal end of the suture thread and the first length of the suture thread which is passing through the third loop of the suture thread;

re-altering the angle between the proximal and the distal segment of the cannula at the hinge of the cannula by manipulating the actuating means of the hinge to withdraw the needle tip and the distal segment of the cannula from the third puncture hole to the first side of the structure; and reducing the third loop of suture thread on the opposite side of the structure by rewinding the suture thread on the spool and generating the tension in a second stitch that passes through the second puncture hole and the third puncture hole, wherein the second stitch is formed by the interlocking of the first length of the suture thread and the third loop of the suture thread in the third puncture hole.

13. The method as claimed in claim 12, further comprising:
securing the suture line on the first side of the structure on finishing the suturing, wherein the distal end of the suture thread and the first length of the suture thread, which is interlocked in a last stitch at a last puncture hole, are released free on the opposite side of the structure; and wherein the suture thread emerging out of the side hole of the cannula is interlocked in the last stitch of the suture line with the first length of the suture thread in the last puncture hole and is pulled to the first side of the structure by rewinding the suture thread on the spool to an extent that part of the first length of the suture thread is withdrawn to the first side of the structure in the form of a new loop of suture thread emerging out of the last puncture hole while the distal end of the suture thread and part of the first length of the suture thread still remain on the opposite side of the structure.

14. The method as claimed in claim 13, further comprising:
restraining the suture thread emerging out of the side hole of the cannula by manipulating the lock-unlock mechanism; and withdrawing the first length of the suture thread and the distal end of the suture thread to the first side of the structure across the last puncture hole by pulling the new loop of the suture thread resulting in the suture thread emerging from the side hole of the cannula interlocking in the penultimate stitch in the penultimate puncture hole.

15. The method as claimed in claim 14, further comprising:
fastening, on the first side of the structure, the first length of the suture thread having the distal end of the suture thread brought to the first side of the structure through the last puncture hole with the suture thread interlocking in the stitch in the penultimate puncture hole and emerging out of the side hole in the cannula; and cutting off excess of the first length of the suture thread and excess of the suture thread emerging out of the side hole in the cannula beyond a region formed by the fastening.

16. The method as claimed in claim 13, wherein finishing the suturing comprises:
cutting the suture thread in a last loop of suture thread on the opposite side of the structure creating a first limb of suture thread and a second limb of suture thread, wherein the first limb of suture thread is created on the opposite side of the structure, passing through the last puncture hole and in continuity with the suture thread on the first side of the structure which is interlocked in the penultimate stitch at the penultimate puncture hole, and the second limb of suture thread is created on an opposite side of the structure, passing through the last puncture hole and in continuity with the suture thread emerging out of the side hole of the cannula on the first side of the structure; and restraining the first limb of suture thread on the opposite side of the structure and rewinding the spool to withdraw the second limb of the suture thread to the first side of the structure across the last puncture hole, wherein the first length of the suture thread and the first limb of suture thread are fastened together on the opposite side of the structure and excess first length of the suture thread and excess first limb of suture thread are cut off beyond a region formed by fastening.

17. The method as claimed in claim 10, further comprising:
positioning the needle tip of the cannula at a second point of the intended suture line on the first side of the structure;

altering the angle between the proximal and the distal segment of the cannula at the hinge of the cannula by manipulating the actuating means to push the needle tip and the side hole through the structure to the opposite side of the structure creating a second puncture hole;

restraining the distal end and the first length of the suture thread on the opposite side of the structure;

pulling the loop of suture thread emerging out of the side hole of the cannula to draw a length of suture thread and form a second loop of the suture thread on the opposite side of the structure, wherein the distal end o f the suture thread and the first length of the suture thread are passed through the second loop of the suture thread;

restraining, on the opposite side of the structure, the distal end of the suture thread and the first length of the suture thread which is passing through the second loop of suture thread and positioning a strengthening material within the second loop of suture thread;

re-altering the angle between the proximal and the distal segment of the cannula at the hinge of the cannula by manipulating the actuating means of the hinge to withdraw the needle tip and the distal segment of the cannula from the second puncture hole to the first side of the structure; and reducing the second loop of the suture thread on the opposite side of the structure by rewinding the suture thread on the spool and generating a tension in a first stitch that passes through the first puncture hole and second puncture hole, wherein the first stitch is formed by the interlocking of the first length of the suture thread and the second loop of the suture thread in the second puncture hole wherein the second loop of the suture thread incorporates the strengthening material on the opposite side of the structure.

18. The method as claimed in claim 17, further comprising:

positioning the needle tip of the cannula at a third point of the intended suture line on the first side of the structure;

altering the angle between the proximal and the distal segment of the cannula at a hinge of the cannula by manipulating the actuating means of the hinge to push the needle tip and the side hole through the structure to the opposite side of the structure creating a third puncture hole;

restraining, on the opposite side of the structure, the distal end of the suture thread and the first length of the suture thread, which is interlocked within the first stitch at the second puncture hole;

pulling the loop of suture thread emerging out of the side hole of the cannula to draw a length of suture thread and form a third loop of the suture thread on the opposite side of the structure, wherein the distal end of the suture thread and the first length of the suture thread are passed through the third loop of the suture thread;

restraining, on the opposite side of the structure, the distal end of the suture thread and the first length of the suture thread which is passing through the third loop of the suture thread and positioning the strengthening material within the third loop of suture thread;

further dispensing the suture thread and re-altering the angle between the proximal and the distal segment of the cannula at the hinge of the cannula by manipulating the actuating means of the hinge to withdraw the needle tip and the distal segment of the cannula from the third puncture hole to the first side of the structure; and reducing the third loop of suture thread on the opposite side of the structure by rewinding the suture thread on the spool and generating required tension in a second stitch that passes through the second puncture hole and the third puncture hole, wherein the second stitch is formed by the interlocking of the first length of the suture thread and the third loop of the suture thread in the third puncture hole wherein the third loop of the suture thread incorporates the strengthening material on the opposite side of the structure.

19. The method as claimed in claim 18, further comprising:

securing the suture line on the opposite side of the structure on finishing the suturing by:

positioning the needle tip of the cannula at a last point of the intended suture line on the first side of the structure;

altering the angle between the proximal and the distal segment of the cannula at a hinge of the cannula by manipulating the actuating means of the hinge to push the needle tip and the side hole through the structure to the opposite side of the structure creating a last puncture hole;

restraining, on the opposite side of the structure, the distal end of the suture thread and the first length of the suture thread, which is interlocked with a penultimate loop of suture thread within which the strengthening material is positioned on the opposite side of the structure at the penultimate puncture hole;

pulling the loop of suture thread emerging out of the side hole of the cannula to draw a length of suture thread and form a last loop of the suture thread and restraining it on the opposite side of the structure;

re-altering the angle between the proximal and the distal segment of the cannula at the hinge by manipulating the actuating means of the hinge to withdraw the needle tip and the distal segment of the cannula from the last puncture hole to the first side of the structure;

cutting the suture thread in the last loop of suture thread to create a first limb of suture thread, on the opposite side of the structure, passing through the last puncture hole and in continuity with the suture thread on the first side of the structure which is interlocked in the penultimate stitch at the penultimate puncture hole, and a second limb of suture thread, on the opposite side of the structure, passing through the last puncture hole and in continuity with the suture thread emerging out of the side hole of the cannula on the first side of the structure; and restraining the first limb of suture thread on the opposite side of the structure and rewinding the spool to withdraw the second limb of the suture thread to the first side of the structure across the last puncture hole, wherein the first length of the suture thread and the first limb of suture thread are fastened together on the opposite side of the structure and excess first length of the suture thread and excess first limb of suture thread are cut off beyond a region formed by fastening.

* * * * *